(12) United States Patent
Walt et al.

(10) Patent No.: US 6,406,845 B1
(45) Date of Patent: *Jun. 18, 2002

(54) FIBER OPTIC BIOSENSOR FOR SELECTIVELY DETECTING OLIGONUCLEOTIDE SPECIES IN A MIXED FLUID SAMPLE

(75) Inventors: David R. Walt, Lexington, MA (US); Brian G. Healey, Guilford, CT (US)

(73) Assignee: Trustees of Tuft College, Medford, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/851,203

(22) Filed: May 5, 1997

(51) Int. Cl.⁷ .......................... C12Q 1/68; G01N 15/06; G01N 21/64; G01N 21/29

(52) U.S. Cl. .......................... 435/6; 435/91.2; 65/409; 250/458.1; 422/68.1; 422/82.05; 422/82.07; 422/82.08; 422/82.09

(58) Field of Search ............................... 422/68.1, 82.05, 422/82.07, 82.08, 82.09; 250/458.1; 65/401; 435/6, 91.2

(56) References Cited

U.S. PATENT DOCUMENTS

| | | | |
|---|---|---|---|
| 4,200,110 A | 4/1980 | Peterson et al. | |
| 4,499,052 A | 2/1985 | Fulwyler | |
| 4,682,895 A | 7/1987 | Costello | |
| 4,785,814 A | 11/1988 | Kane | |
| 4,822,746 A | 4/1989 | Walt | |
| 4,824,789 A | 4/1989 | Yafuso et al. | |
| 4,999,306 A | 3/1991 | Yafuso et al. | |
| 5,002,867 A | 3/1991 | Macevicz | |
| 5,028,545 A | 7/1991 | Soini | |
| 5,105,305 A | 4/1992 | Betzig et al. | |
| 5,114,864 A | 5/1992 | Walt | |
| 5,132,242 A | 7/1992 | Cheung | |
| 5,143,853 A | 9/1992 | Walt | |
| 5,194,300 A | 3/1993 | Cheung | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,254,477 A | 10/1993 | Walt | |
| 5,298,741 A | 3/1994 | Walt et al. | |
| 5,302,509 A | 4/1994 | Cheeseman | |
| 5,320,814 A * | 6/1994 | Walt et al. ............... | 422/82.07 |
| 5,357,590 A | 10/1994 | Auracher | |
| 5,380,489 A | 1/1995 | Sutton et al. ............. | 422/68.1 |
| 5,435,724 A | 7/1995 | Goodman et al. | |
| 5,481,629 A | 1/1996 | Tabuchi | |
| 5,494,798 A * | 2/1996 | Gerdt et al. ................ | 435/6 |
| 5,496,997 A | 3/1996 | Pope | |
| 5,512,490 A | 4/1996 | Walt et al. | |
| 5,516,635 A | 5/1996 | Ekins et al. | |
| 5,565,324 A | 10/1996 | Still et al. | |
| 5,573,909 A | 11/1996 | Singer et al. | |
| 5,575,849 A | 11/1996 | Honda et al. | |
| 5,633,972 A | 5/1997 | Walt et al. | |
| 5,639,603 A | 6/1997 | Dower et al. | |
| 5,656,241 A | 8/1997 | Seifert et al. | |
| 5,690,894 A * | 11/1997 | Pinkel et al. ............... | 422/68.1 |
| 5,814,524 A | 10/1998 | Walt | |
| 5,840,256 A | 11/1998 | Demers et al. | |
| 5,854,684 A | 12/1998 | Stabile et al. | |
| 5,863,708 A | 1/1999 | Zanzucchi et al. | |
| 5,888,723 A | 3/1999 | Sutton et al. ................ | 435/5 |
| 5,900,481 A | 5/1999 | Lough et al. .............. | 536/55.3 |
| 6,023,540 A | 2/2000 | Walt et al. | |

FOREIGN PATENT DOCUMENTS

| | | |
|---|---|---|
| EP | 0269764 | 6/1988 |
| EP | 0 392 546 | 10/1990 |
| EP | 0478319 | 4/1992 |
| EP | 0723146 | 7/1996 |
| WO | 89/11101 | 11/1989 |
| WO | 93/02360 | 2/1993 |
| WO | 96/03212 | 2/1996 |
| WO | 97/14028 | 4/1997 |
| WO | 97/40385 | 10/1997 |
| WO | 98/40726 | 9/1998 |
| WO | 98/50782 | 11/1998 |
| WO | 98/53093 | 11/1998 |
| WO | 98/53300 | 11/1998 |

OTHER PUBLICATIONS

Ferguson et al, "A fiber optic DNA biosensor microarray for the analysis of Gene expression", Nature Biotechnology 14:1681–1684, Dec. 1996.*

Healy et al, "Fiberoptic DNA sensor capable of detecting point mutations", Anal. Biochem. 251:270–279, Sep. 1997.*

Strachan et al, "A rapid general method for the identification of PCR products using a fibre–optic biosensor and its application to the detection of Listeria", Letters Appl. Microbiol. 21:5–9, 1995.*

(List continued on next page.)

Primary Examiner—Jeffrey Fredman
(74) Attorney, Agent, or Firm—Robin M. Silva; Flehr Hohbach Test Albritton & Herbert LLP

(57) ABSTRACT

The present invention provides biosensors, apparatus and methods for selectively detecting at least one complementary oligonucleotide target specie in a fluid sample containing a mixture of different oligonucleotide fragments. One preferred embodiment of the biosensor is as a unitary fiber optic array having an in-situ hybridization zone comprising not less than one specie of single stranded oligonucleotide disposed as individual deposits in aligned organization upon multiple strand end faces at differing spatial positions on the distal array end surface. In this manner, a collective of deployed, single specie, multiple fixed probes are presented for selective in-situ hybridization on-demand with at least one mobile complementary target specie ultimately bearing a joined identifying label. The biosensor provides for optical detection of in-situ hybridization on the distal end surface via the presence of the concomitantly disposed joined identifying label at the differing spatial positions.

30 Claims, 19 Drawing Sheets

OTHER PUBLICATIONS

Abel et al, "Fiber–Optic evanescent wave biosensor for the detection of oligonucleotides", Anal. Chem. 68:2905–2912, Sep. 1996.*

Piunno et al, "Fiber–optic DNA sensor for fluorometric nucleic acid determination", Anal. Chem. 67:2635–2643, Aug. 1995.*

Barnard et al., "A Fibre–Optic Chemical Sensor with Discrete Sensing Sites," Nature, 353:338–340 (Sep. 1991).

Fuh et al., "Single Fibre Optic Fluorescence pH Probe," Analyst, 112:1159–1163 (1987).

Grazier et al., "In–vivo Biomedical Monitoring by Fiber–Optic Systems," Journal of Lightwave Technology, 13(7):13936–1406 (1995).

Healey et al., "Fiberoptic DNA Sensor Array Capable of Detecting Point Mutations," Analytical Biochemistry, 251:270–279 (1997).

Hirschfeld et al., "Laser–Fiber–Optic "Optrode" for Real Time in Vivo Blood Carbon Dioxide Level Monitoring," Journal of Lightwave Technology, LT–5(7):1027–1033 (1987).

Peterson et al., "Fiber–Optic Sensors for Biomedical Applications,"Science, 13:123–127 (1984).

Anonymous,"Fluorescent Microspheres," Tech. Note 19, Bang Laboratories, (Fishers,In) Feb. 1997.

Anonymous, "Microsphere Selection Guide," Bang Laboratories, (Fisher,In) Sep. 1998.

Bangs, L. B., "Immunological Applications of Microspheres," The Latex Course, Bangs Laboratories (Carmel, IN) Apr. 1996.

Peterson, J. et al., "Fiber Optic pH Probe for Physiological Use," Anal. Chem., 52:864–869 (1980).

Pope, E. "Fiber Optic Chemical Microsensors Employing Optically Active Silica Microspehres," SPIE, 2388:245–256 (1995).

Pantano et al., "Analytical Applications of Optical Imaging Fibers," *Anal. Chem.*, 67:481A–487A (1995).

Walt, "Fiber–Optic Sensors for Continuous Clinical Monitoring," Proc. IEEE, 80(6): 903–911 (1992).

Drmanac, R. et al., "Sequencing by Oligonucleotide Hybridization: A Promising Framework in Decoding of the Genome Program," The First International Conference on Electrophoresis, Supercomputing and the Human Genome, Proceeding os th Apr. 10–13, 1990 Conference at Florida State University. Ed. C. Cantor and H. Lim.

Drmanac, R. et al., "Prospects for a Miniaturized, Simplified and Frugal Human Genome Project," Scientia Yugoslavica, 16(1–2):97–107 (1990).

Drmanac, R. et al., "Sequencing by Hybridization (SBH) with Oligonucleotide Probes as an Integral Approach for the Analysis of Complex Genomes," International Journal of Genome Research, 1(1):59–79 (1992).

Drmanac, R. et al., "Sequencing by Hybridization," Automated DNA Sequencing and Analysis, ed. M. Adams, C. Fields and J. Venter. (1994).

Healey et al., "Improved Fiber–Optic Chemical Sensor for Penicillin," Anal. Chem. 67(24):4471–4476 (1995).

Healey et al., "Development of a Penicillin Biosensor Using a Single Optical Imaging Fiber," SPIE Proc. 2388:568–573 (1995).

Michael et al., "Making Sensors out of Disarray: Optical Sensor Microarrays," Proc. SPIE, 3270: 34–41 (1998).

Michael et al., "Randomly Ordered Addressable High–Density Optical Sensor Arrays," Anal. Chem. 70(7): 1242–1248 (Apr. 1998).

Michael et al., "Fabrication of Micro–and Nanostructures Using Optical Imaging Fibers and there Use as Chemical Sensors," Proc. 3rd Intl. Symp., Microstructures and Microfabricated Systems, ed. P. J. Hesketh, et al., v. 97–5, Electrochem. Soc., 152–157 (Aug. 1997).

* cited by examiner

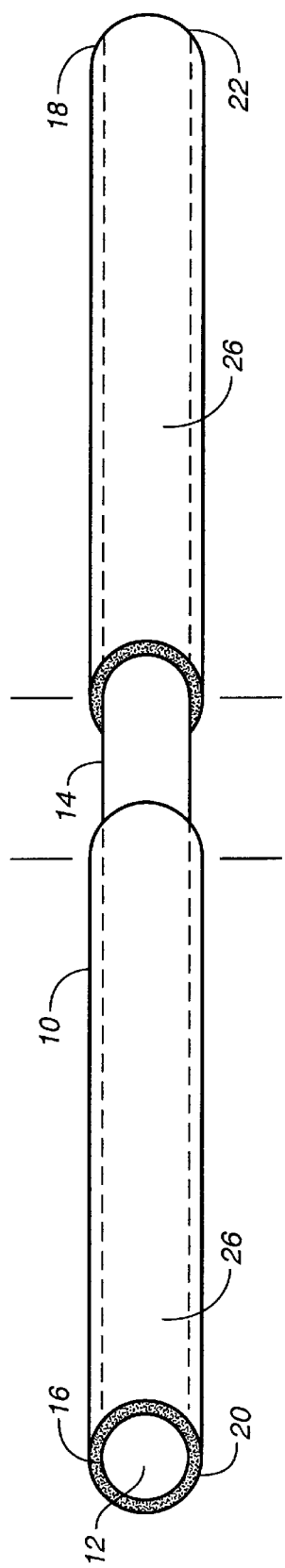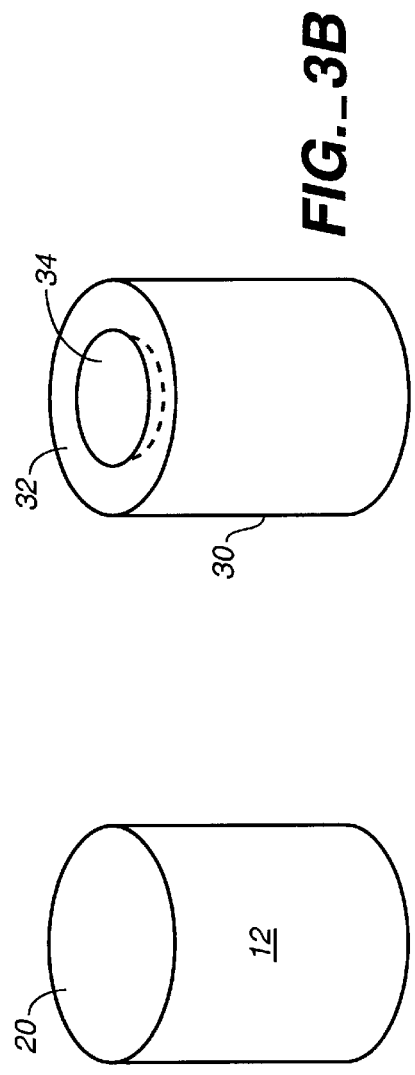

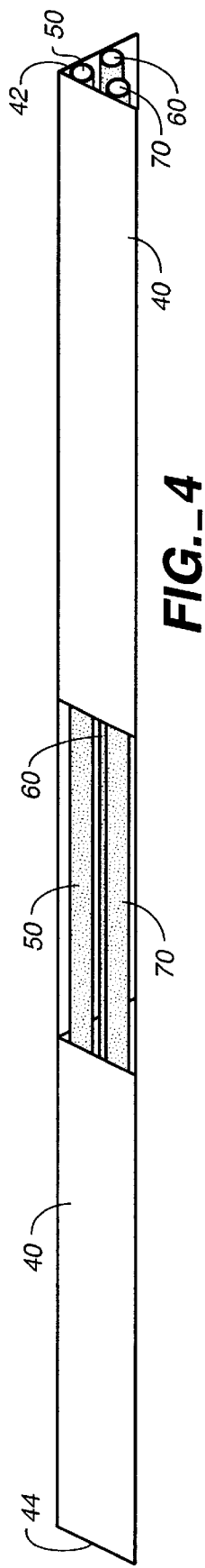
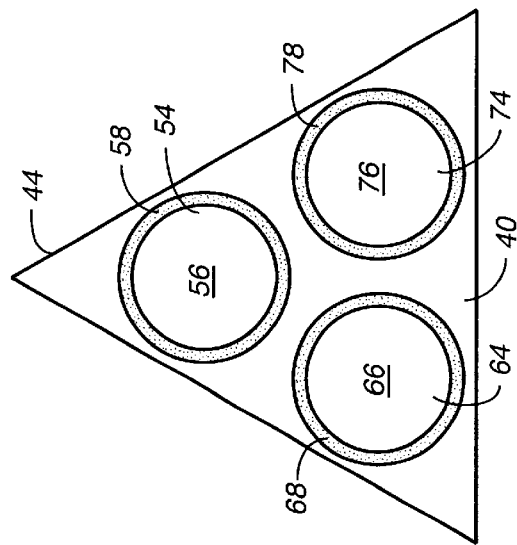
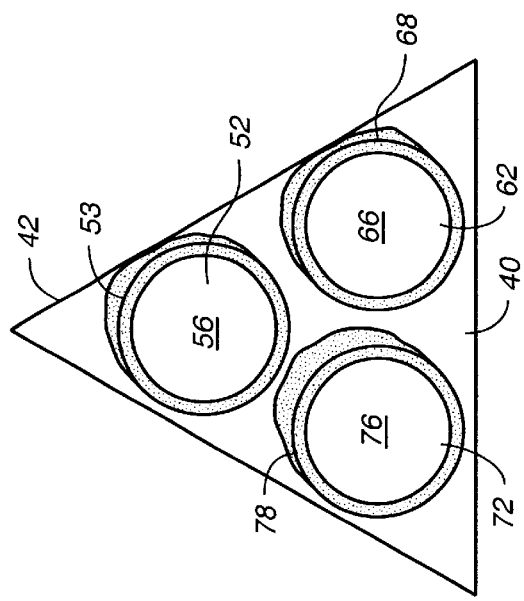

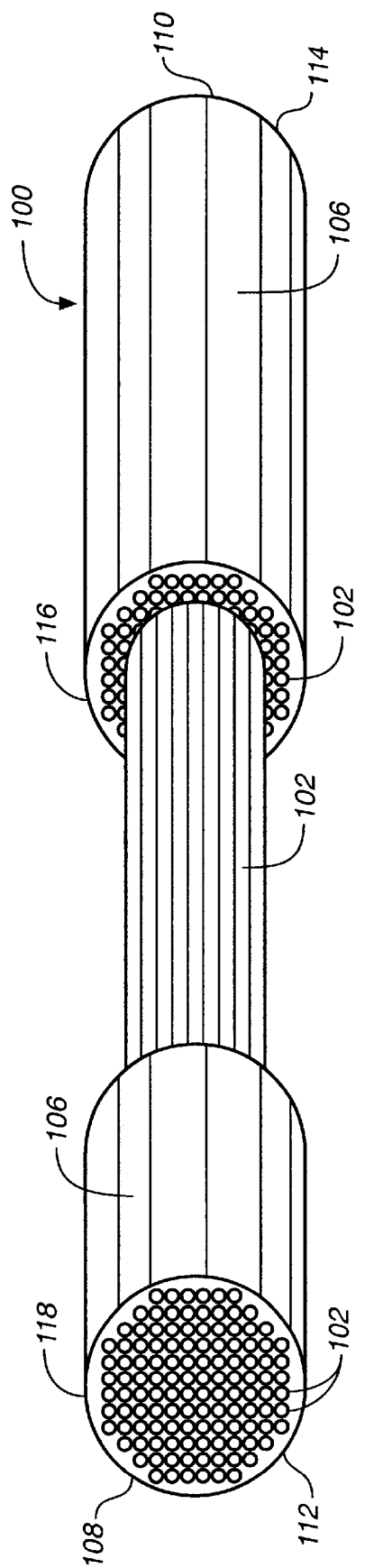
FIG._6

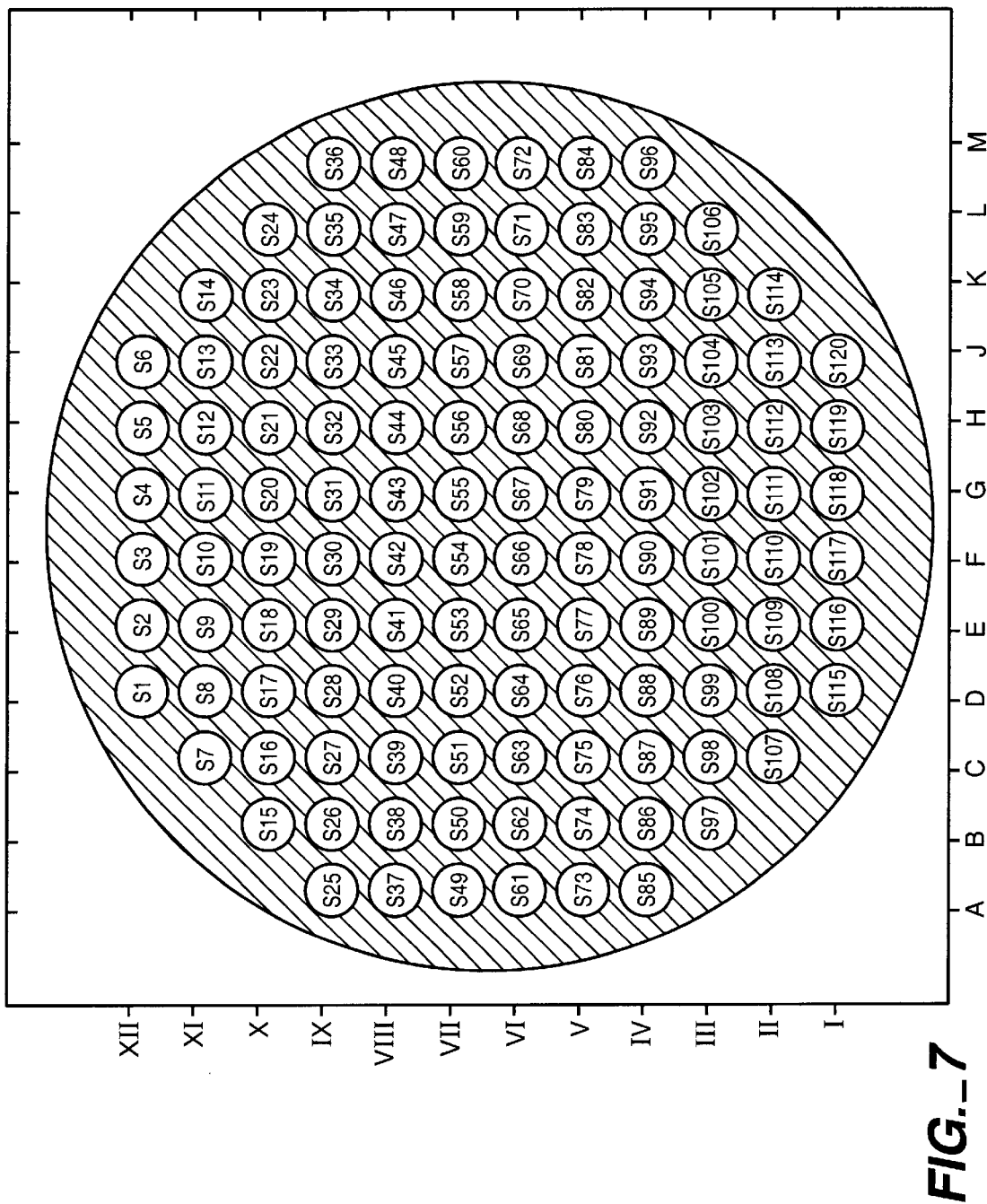
FIG._7

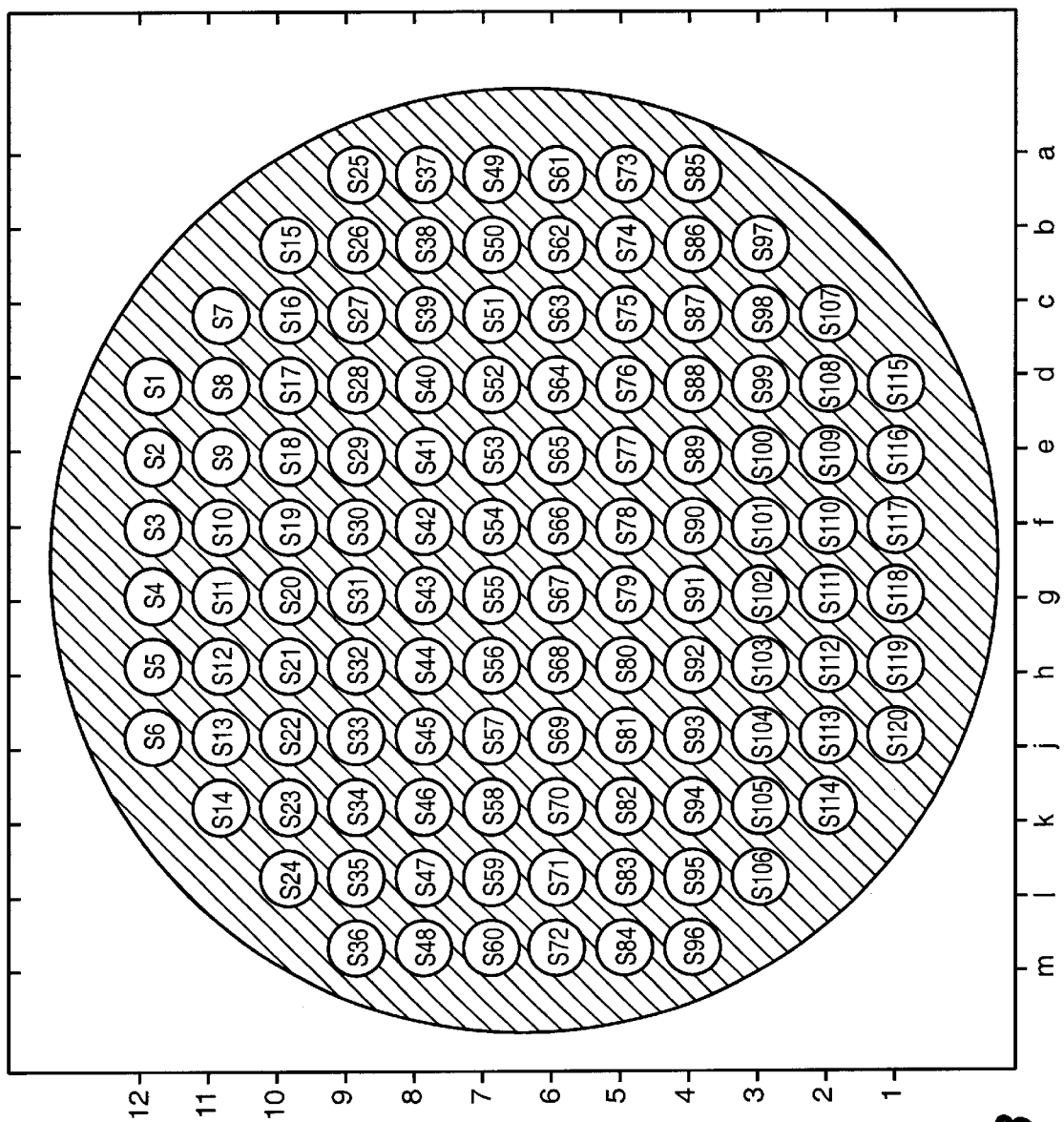
FIG._8

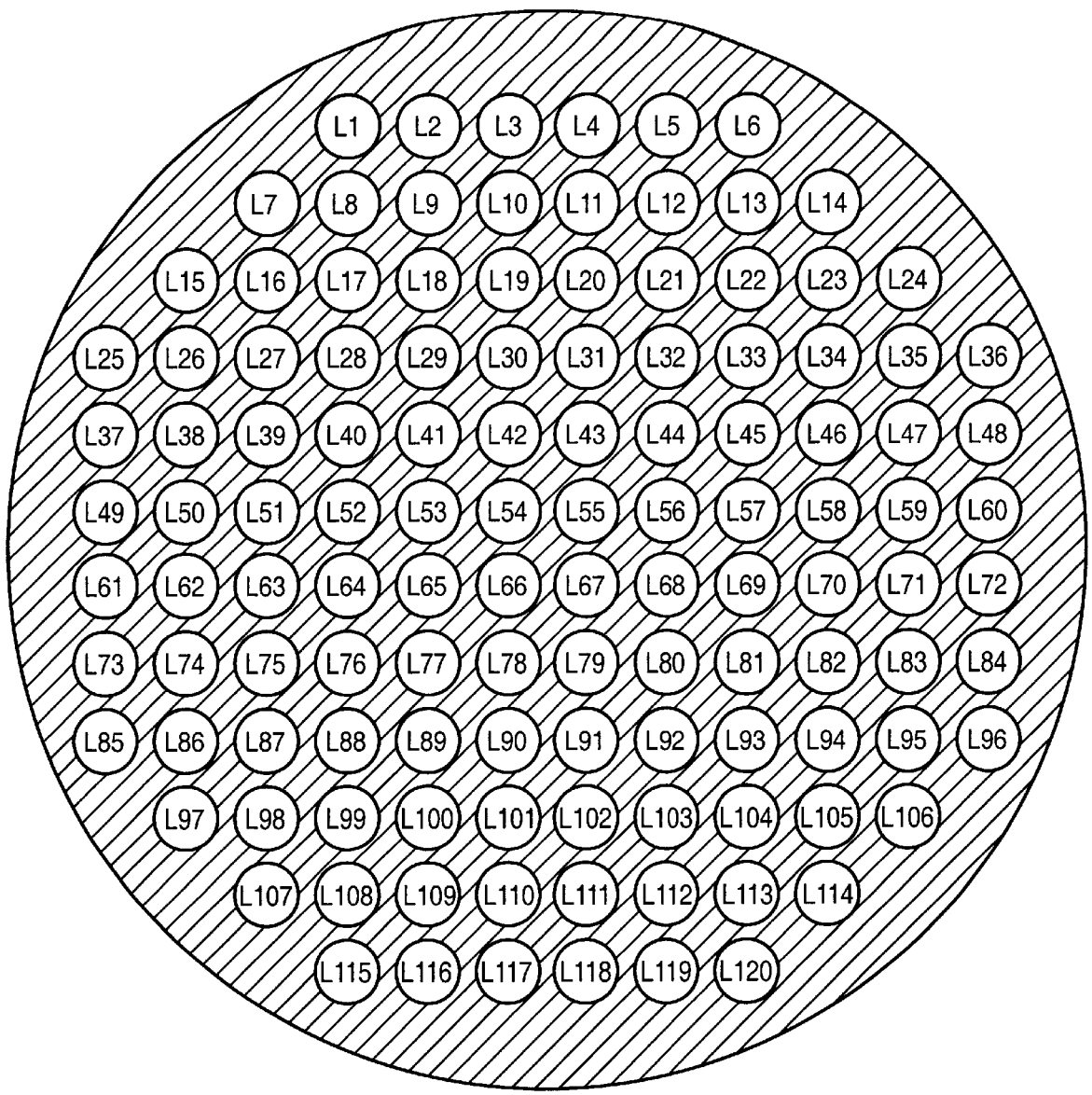
FIG._9

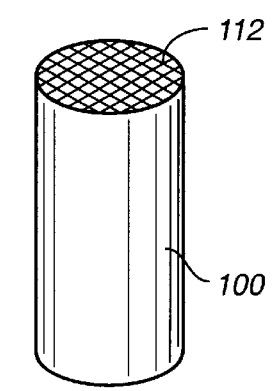
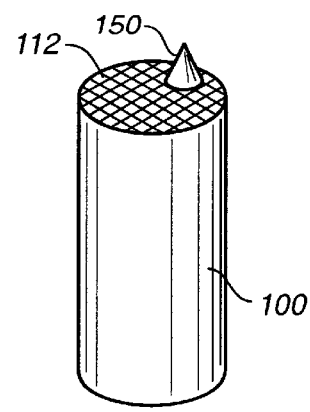
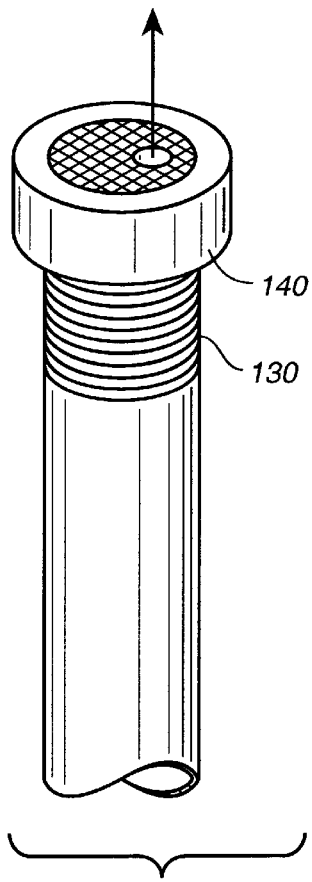
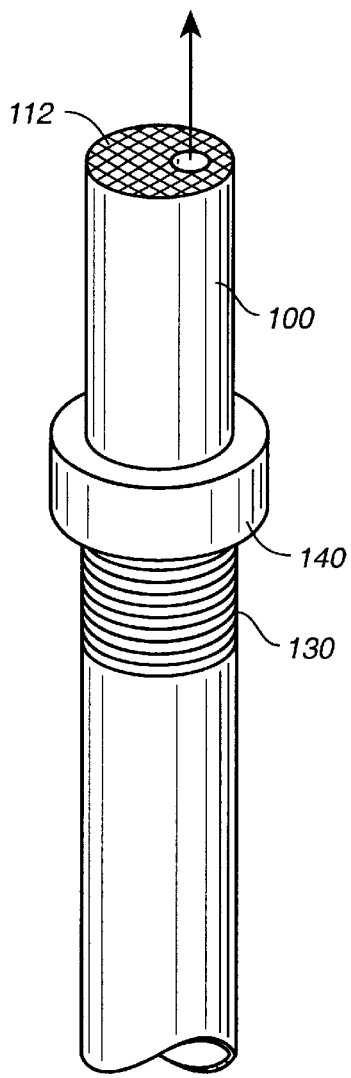
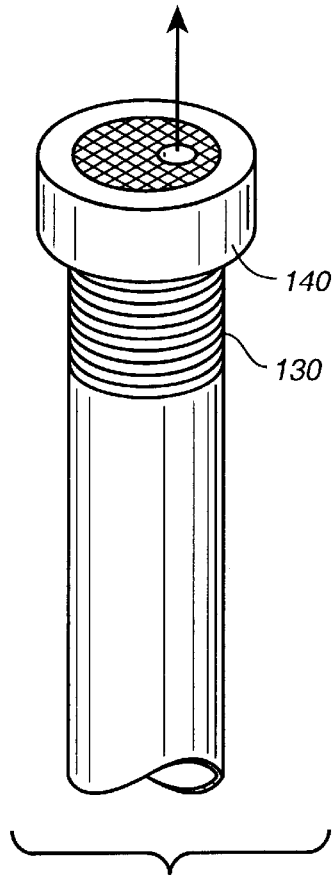
FIG._10  FIG._11  FIG._12

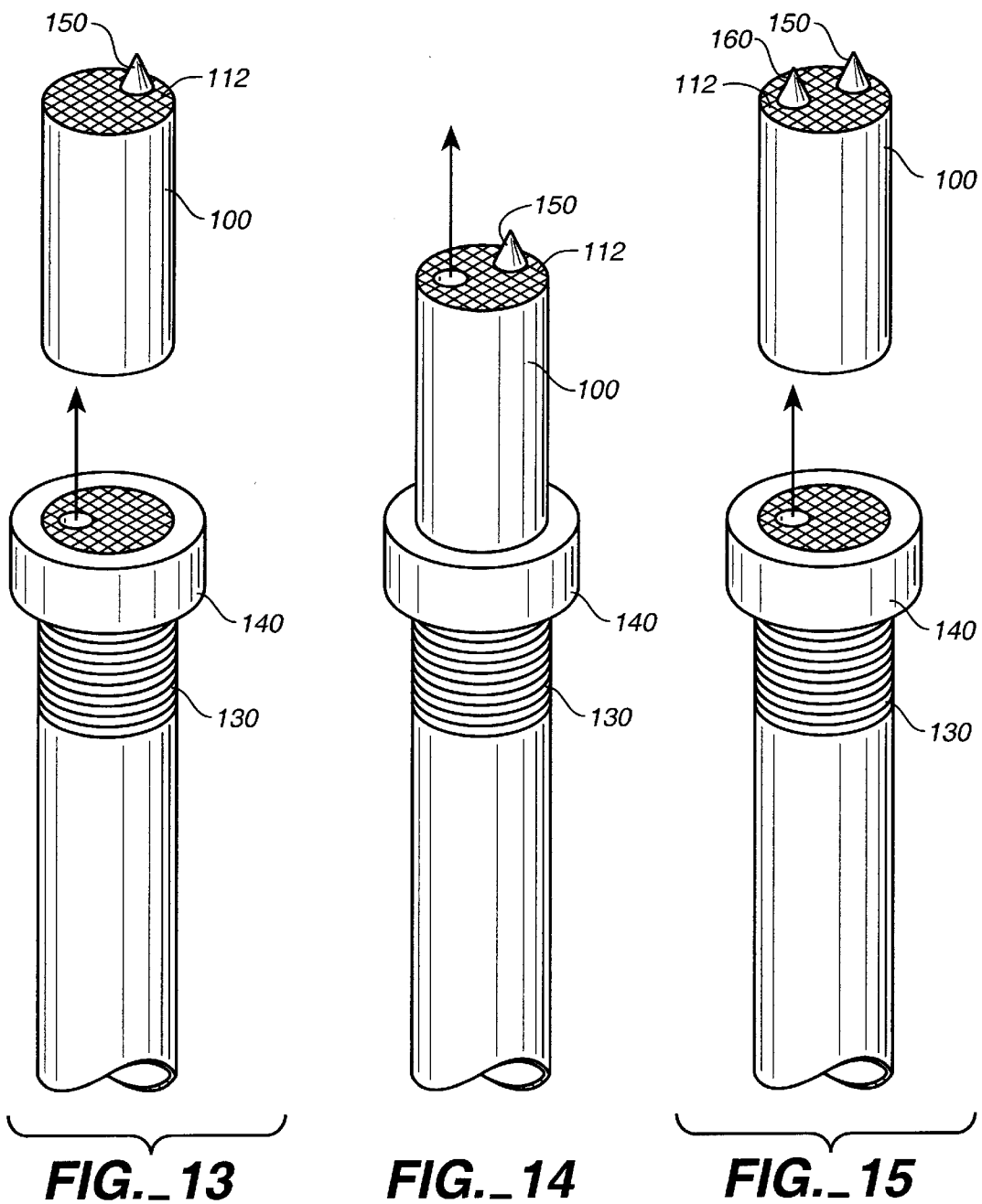
FIG._13   FIG._14   FIG._15

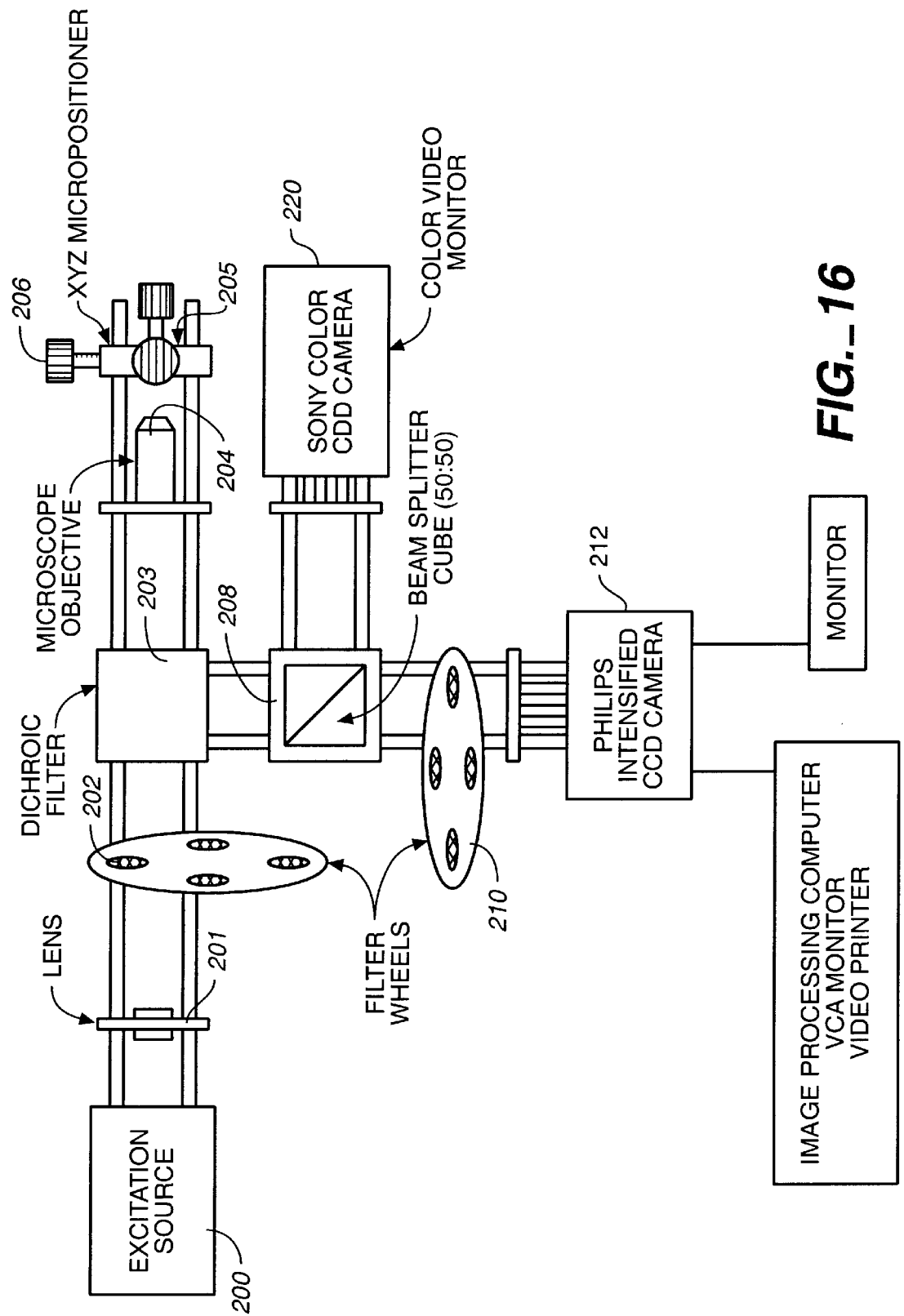
FIG._16

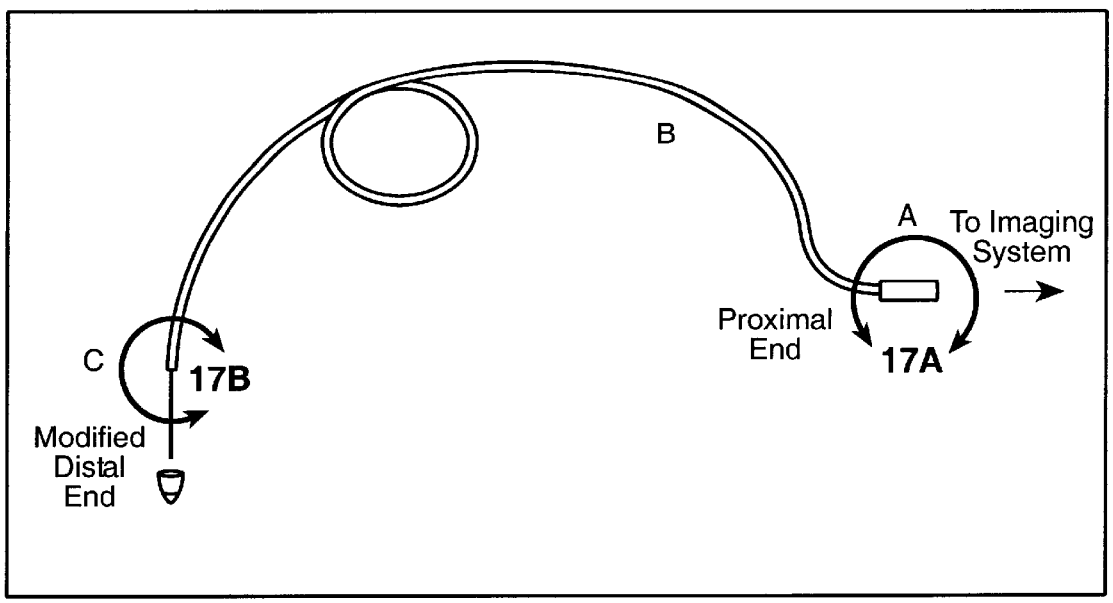
FIG._17
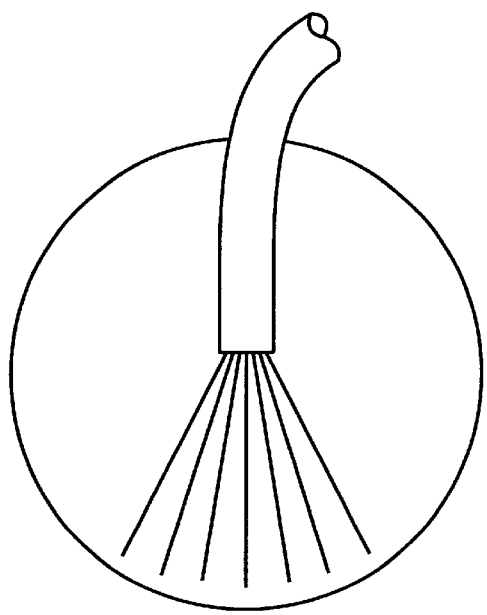
FIG._17B
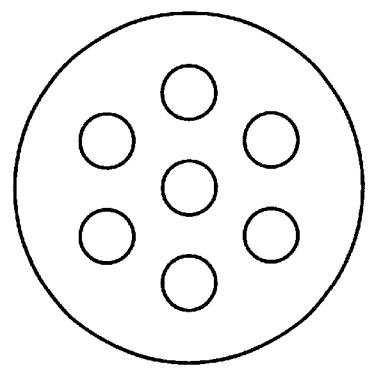
FIG._17A

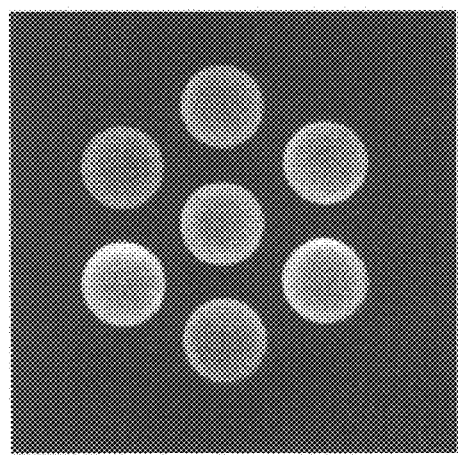
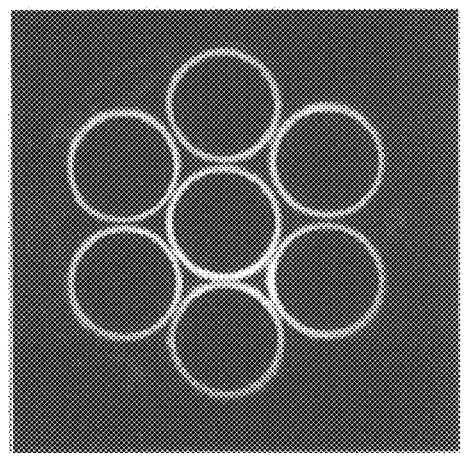
FIG._18A    FIG._18B
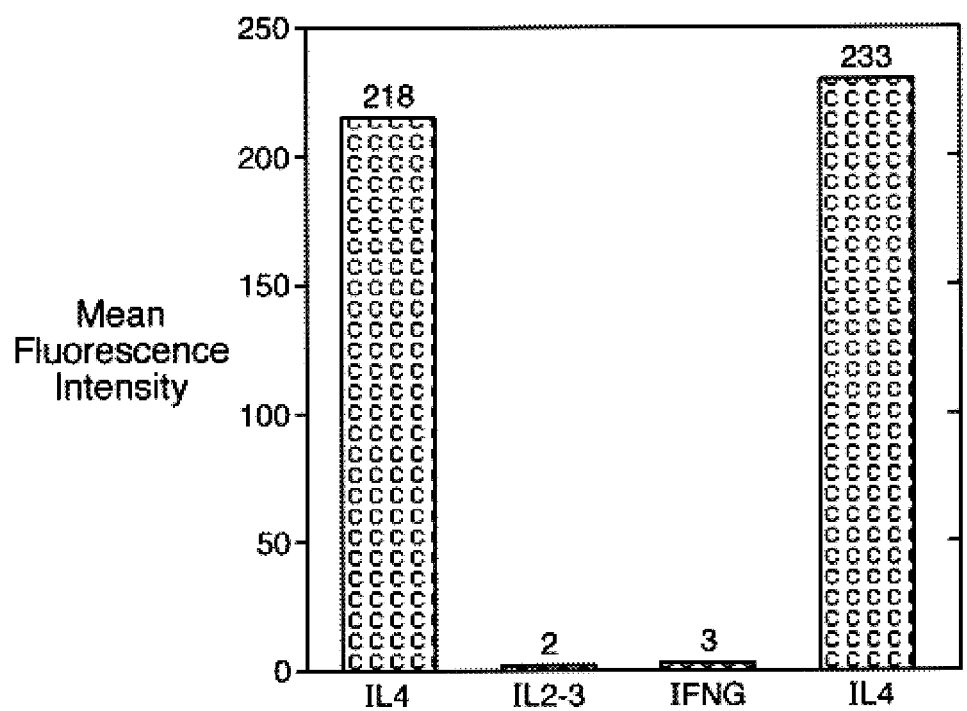
FIG._19    Target Solution

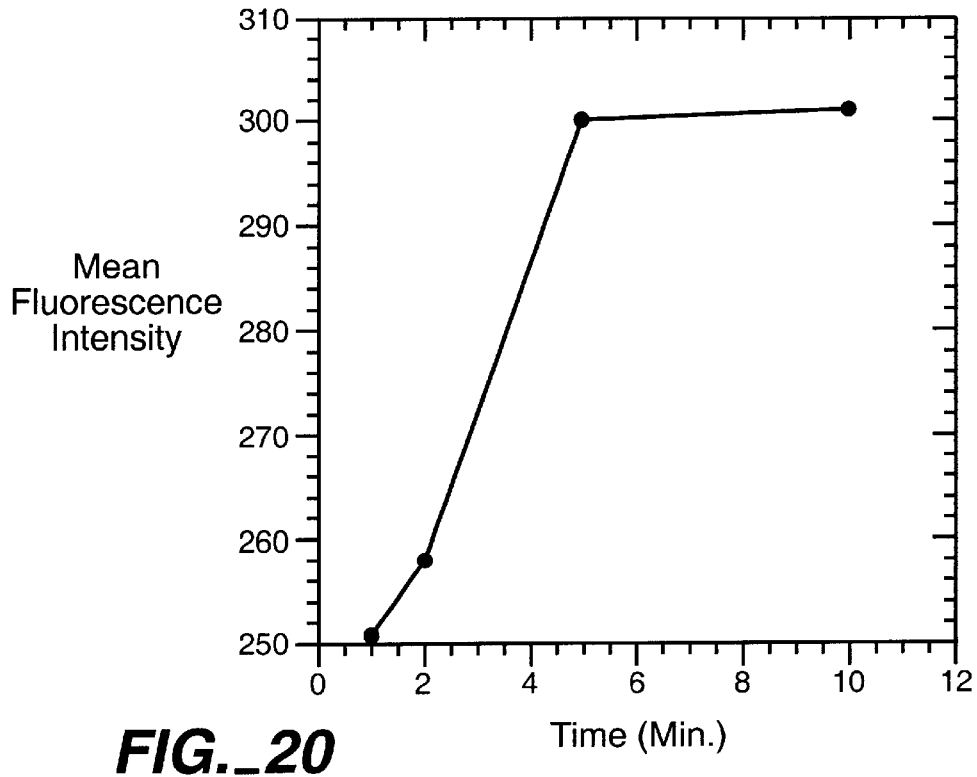
FIG._20
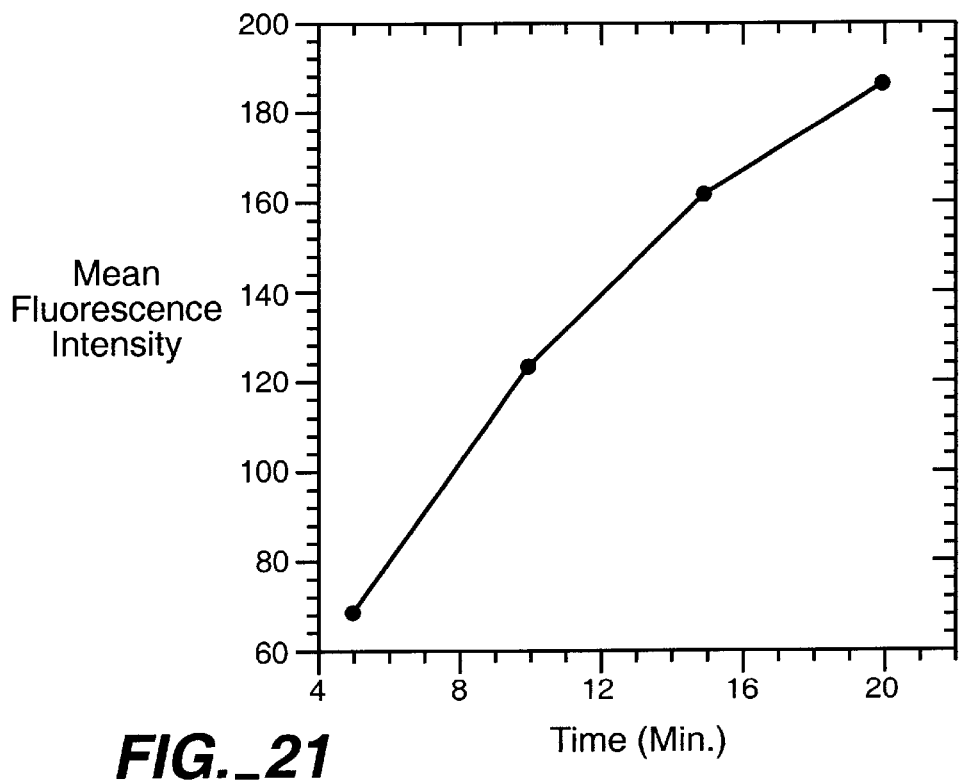
FIG._21

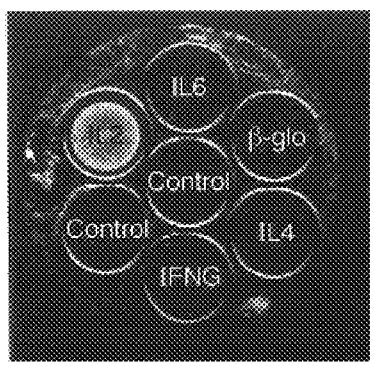
FIG._22A
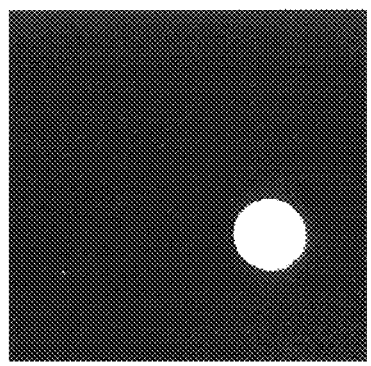
FIG._22B
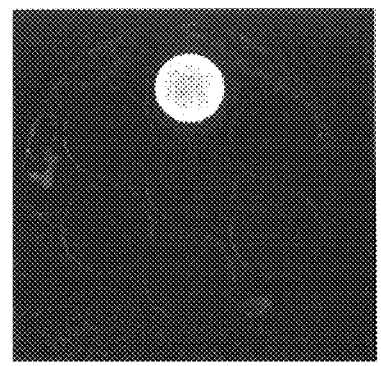
FIG._22C
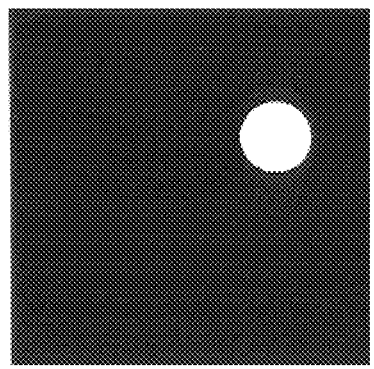
FIG._22D
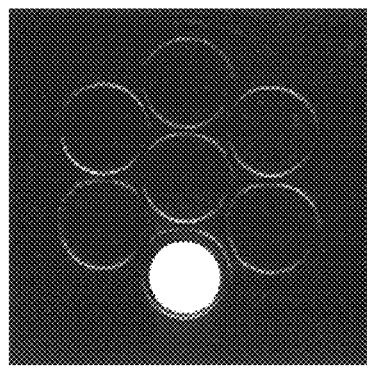
FIG._22E
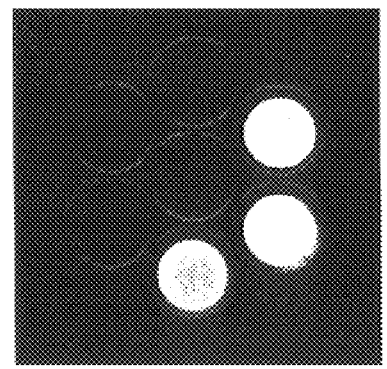
FIG._22F

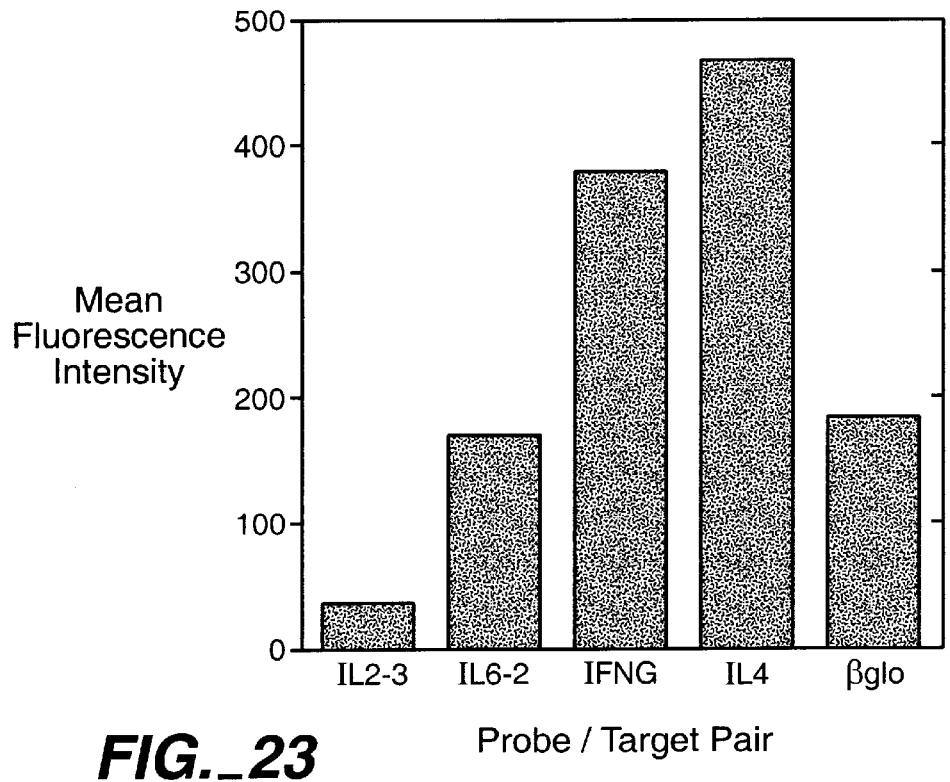
FIG._23
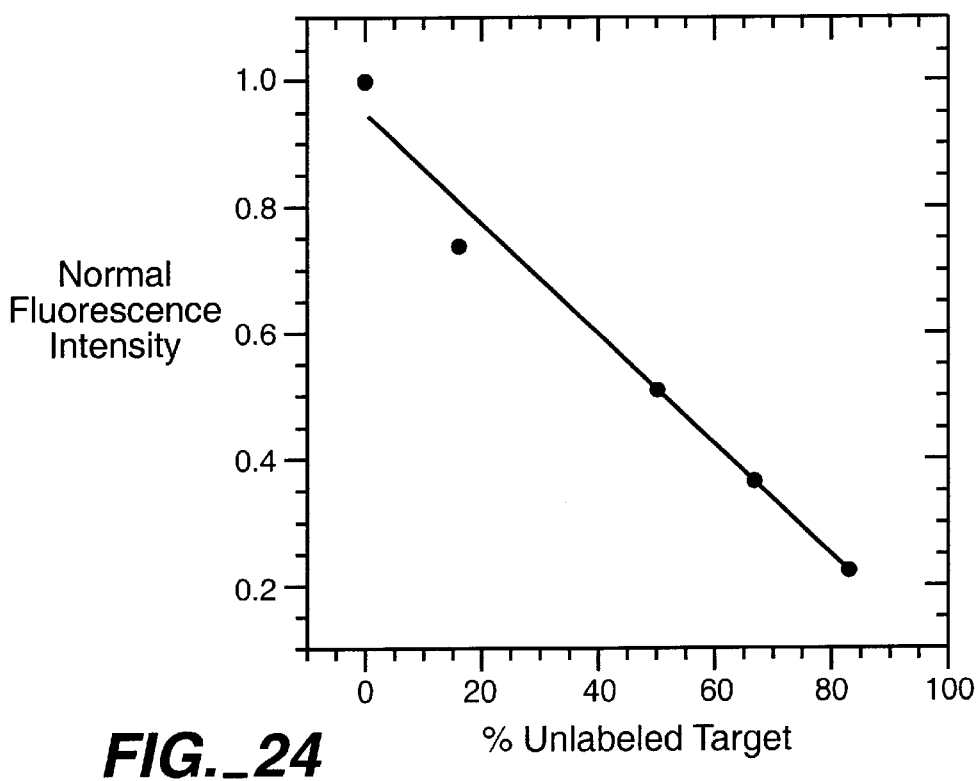
FIG._24

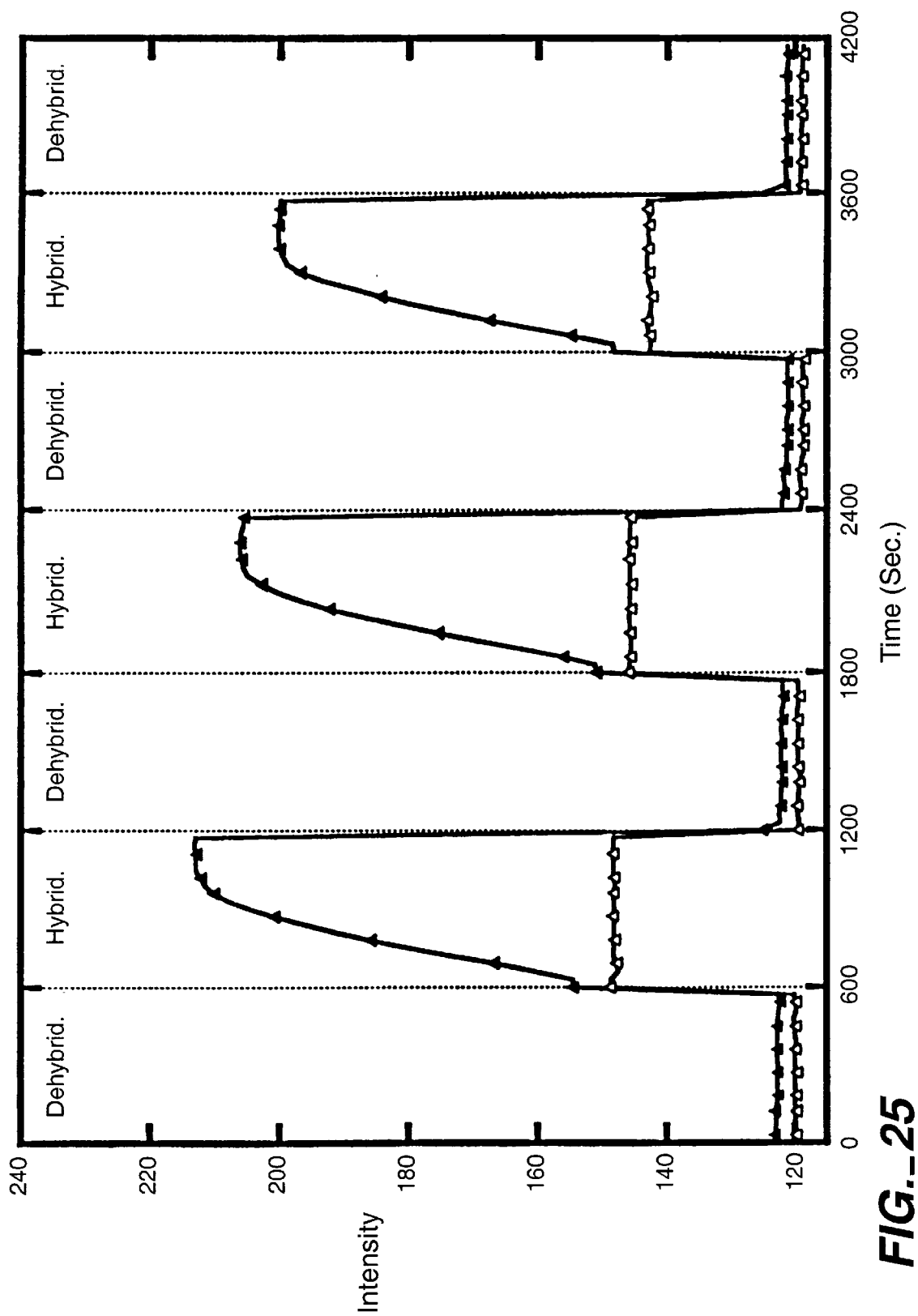
FIG._25

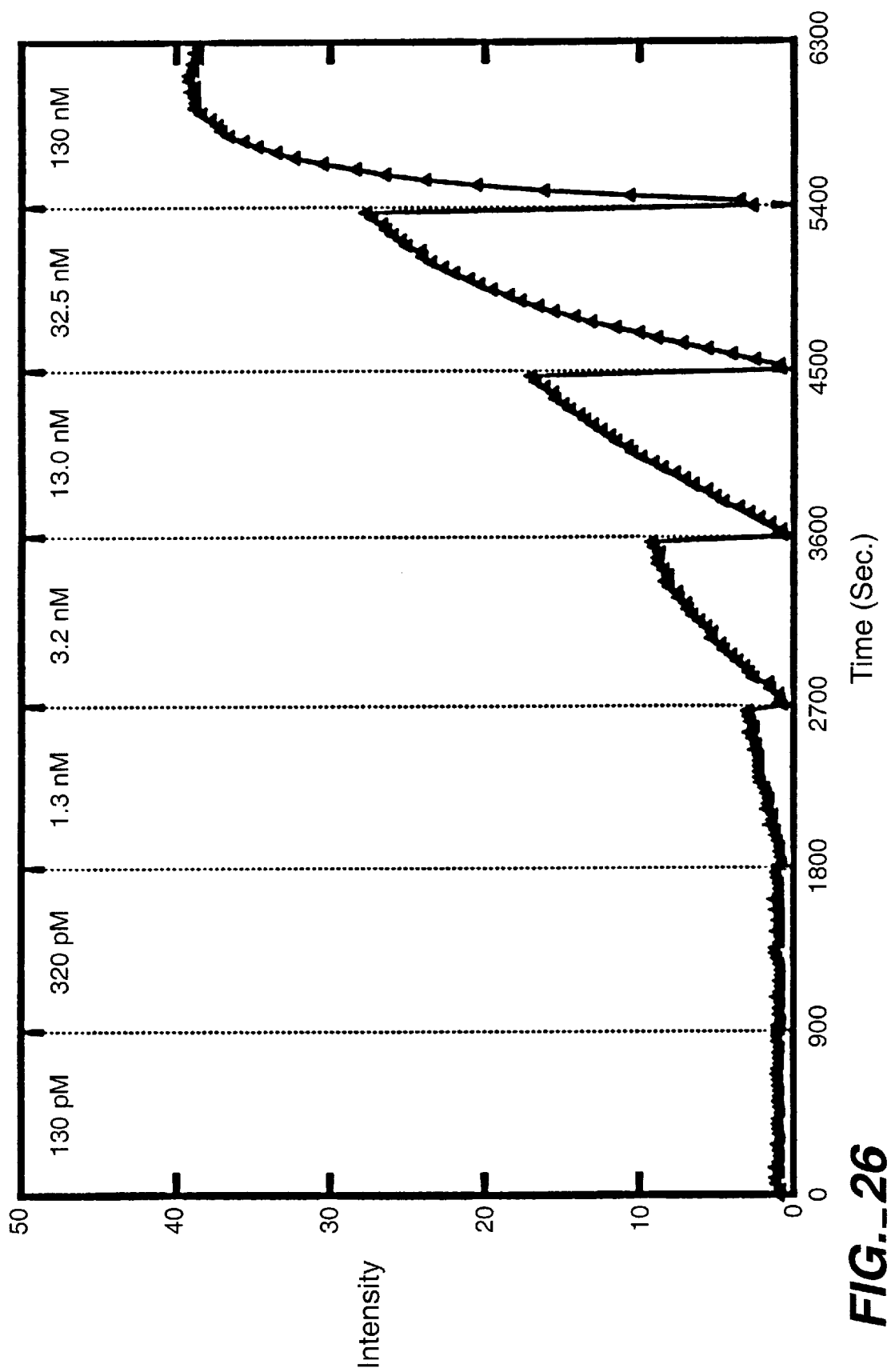
FIG._26

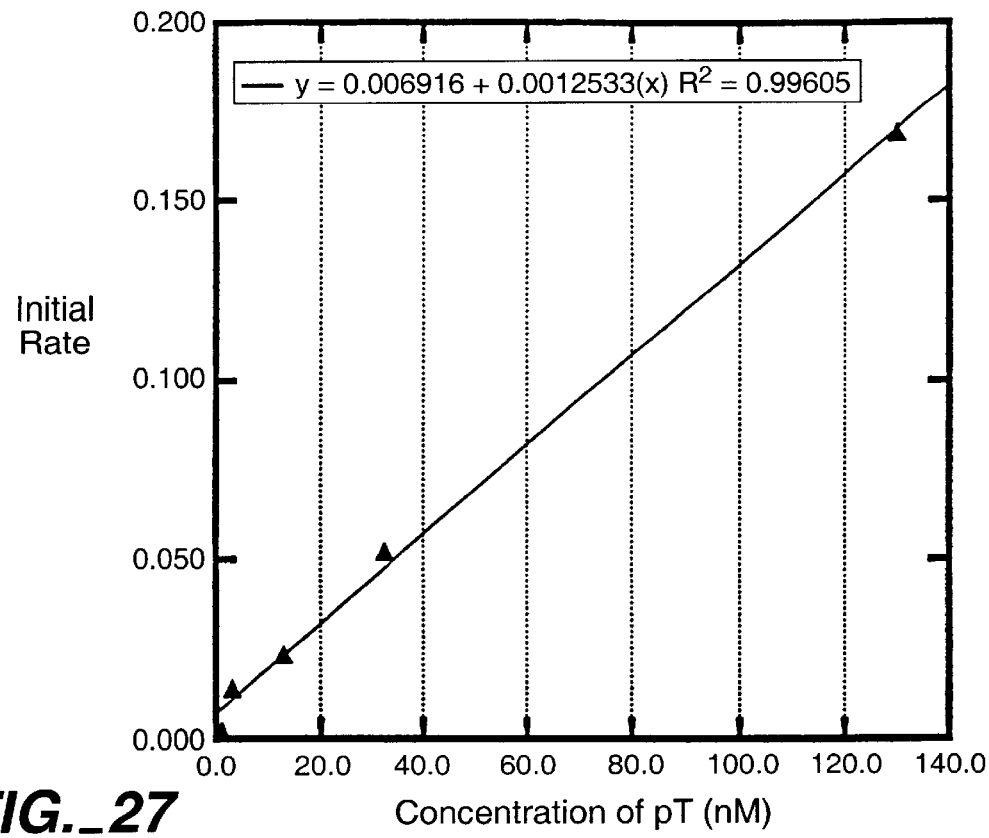
FIG._27
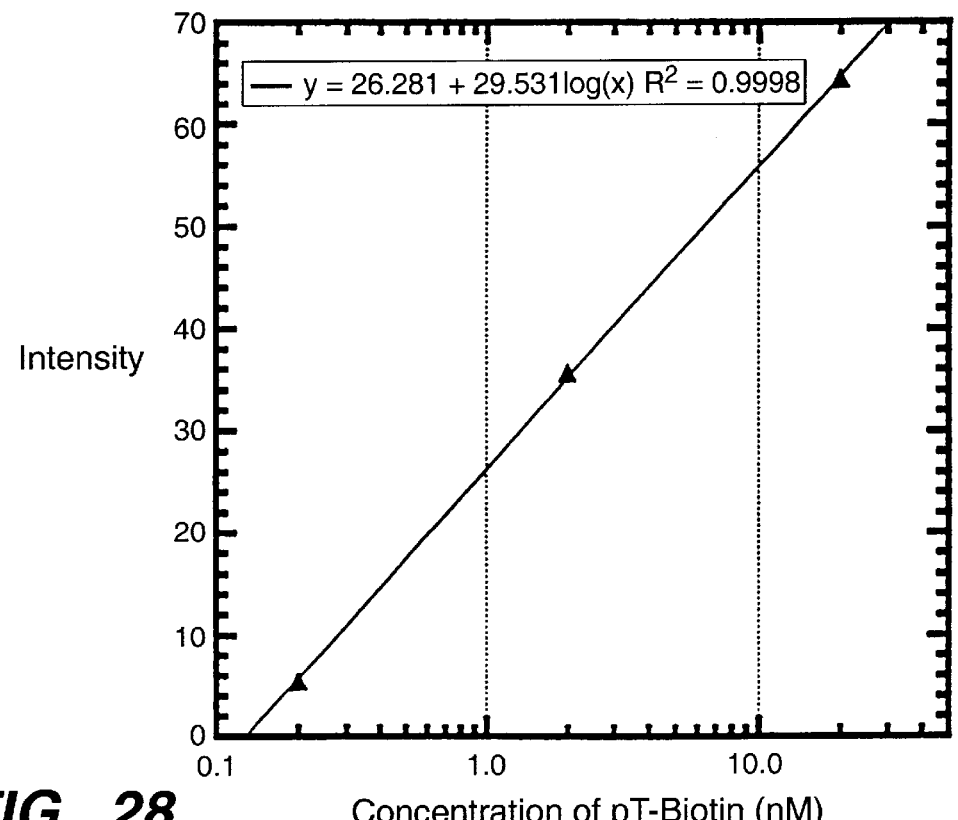
FIG._28

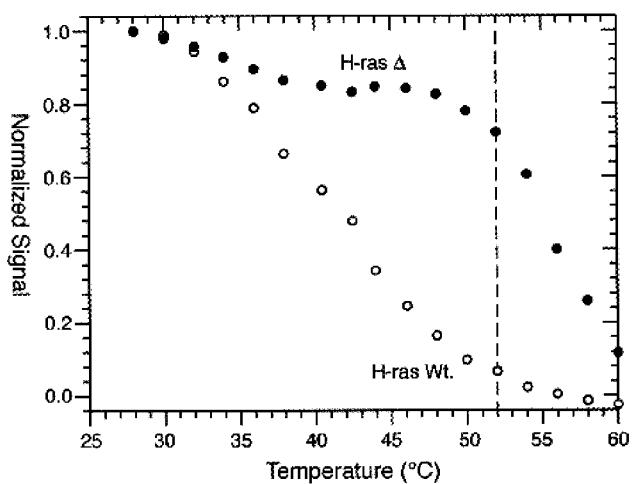
FIG._29
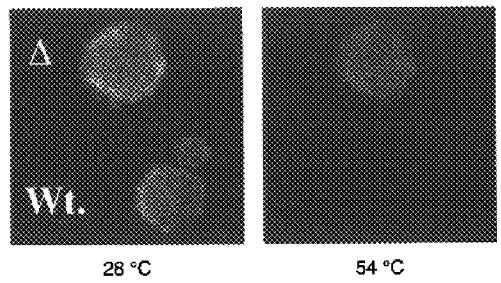
28 °C  54 °C
FIG._30A  FIG._30B
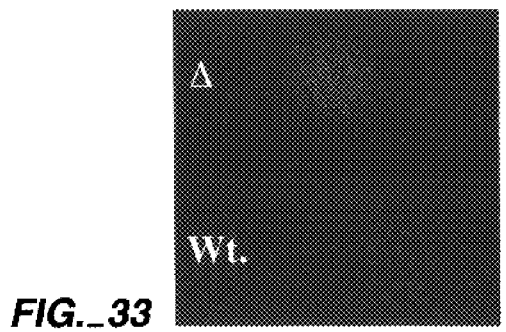
FIG._33

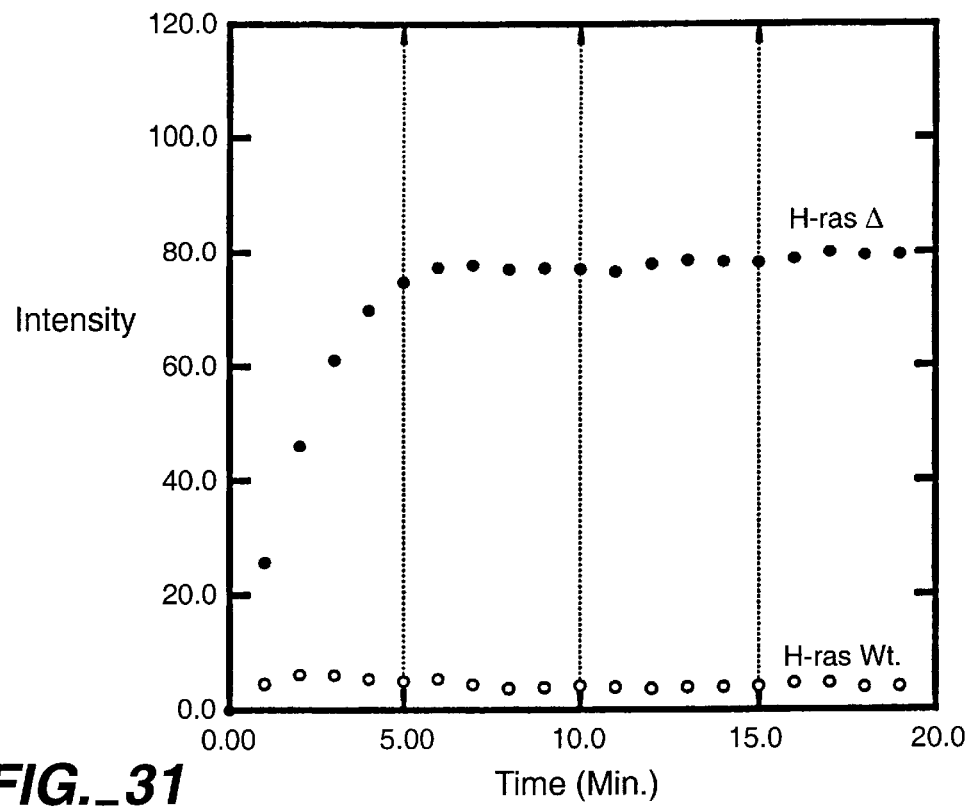
FIG._31
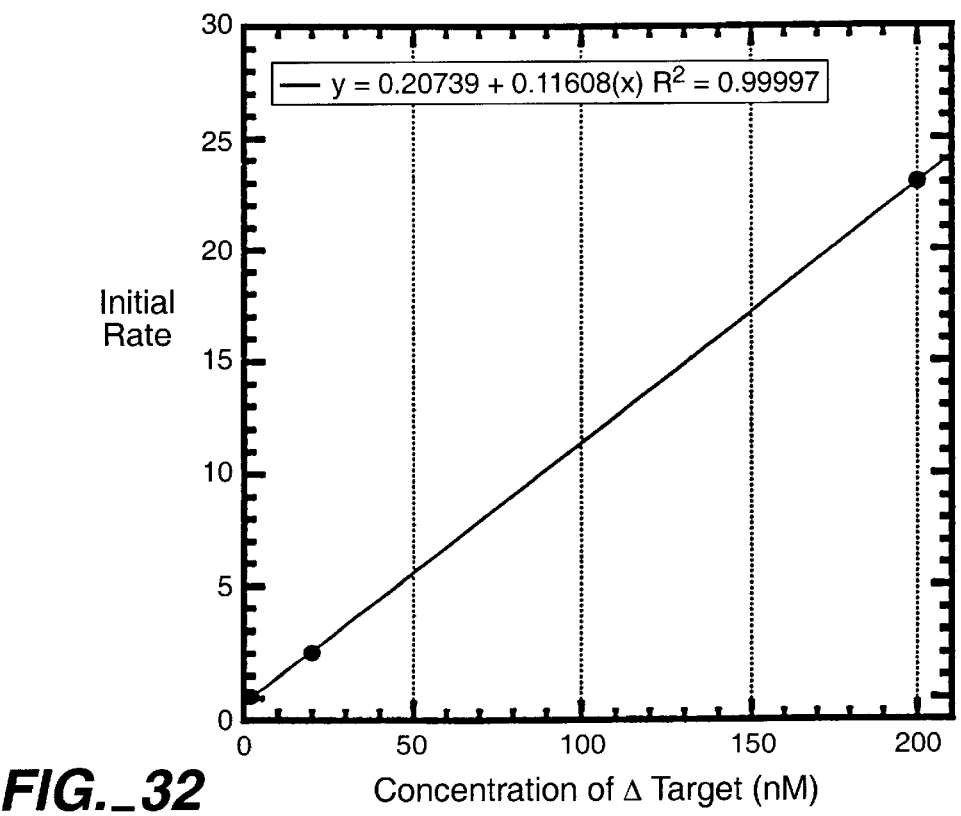
FIG._32

FIBER OPTIC BIOSENSOR FOR SELECTIVELY DETECTING OLIGONUCLEOTIDE SPECIES IN A MIXED FLUID SAMPLE

RESEARCH SUPPORT

The research for the present invention was supported by a grant from the National Institutes Of Health under contract grant GM 48142.

FIELD OF THE INVENTION

The present application is concerned generally with apparatus and methods for the analysis of genes and gene expression; and is particularly directed to the construction and use of a fiber optic biosensor able to detect selectively one or multiple DNA, RNA, or PNA oligonucleotide fragments concurrently.

BACKGROUND OF THE INVENTION

In less than twenty years, the field of molecular genetics, including the specialty of genetic engineering, has revolutionized the science of biology as a whole and is in the process of restructuring medicine in both diagnostic and therapeutic applications. Not only are individual genes now being isolated and characterized, but also extensive research studies as to how genes function and are regulated in-vivo are being actively pursued. Moreover, many techniques for manipulating and modifying genes have been reported and are today becoming widespread in use and diverse in application. Merely exemplifying the many authoritative texts and published articles presently available in the literature regarding genes, gene manipulation and genetic analysis are the following: *Gene Probes for Bacteria* (Macario and De Macario, editors) Academic Press Inc. 1990; *Genetic Analysis, Principles Score and Obiectives* by John R. S. Fincham, Blackwell Science Ltd., 1994; *Recombinant DNA Methodology II* (Ray Wu, editor), Academic Press, 1995; *Molecular Cloning. A Laboratory Manual* (Maniatis, Fritsch, and Sambrook, editors), Cold Spring Harbor Laboratory, 1982; *PCR (Polymerase Chain Reaction)*, (Newton and Graham, editors), Bios Scientific Publishers, 1994; and the many references individually cited within each of these publications.

Among the many innovative ideas and novel techniques generated by molecular genetic research studies has been the generation of nucleic acid probes for identifying the existence of specific genes, the products of gene expression, and the presence of mutations in one or more genes. By definition, a nucleic acid probe is a DNA or RNA oligonucleotide fragment or peptide nucleic acid (PNA) of known base sequence. Existing as a single-stranded segment of base codons, a nucleic acid probe which will bind to a complementary base sequence of nucleic acids which is the analyte of interest for any purpose. Thus, the oligonucleotide probe, via its selective binding capability, is employed to detect and identify individual gene fragments or nucleic acid sequences present in viruses, bacteria, and other cells serving as samples for scientific, research or medical interest.

In general, any DNA, RNA, or PNA sequential fragment (obtained from any source and regardless of whether the sequence is naturally occurring or synthetically prepared) must meet two essential criteria in order to be truly useful as an oligonucleotide probe. First, the oligonucleotide probe sequence must be as specific as possible for the intended complementary target sequence; and, preferably, bind exclusively with only the complementary target sequence with little or no cross-reaction. Secondly, the oligonucleotide probe must be able to distinguish among closely related nucleic acid base sequences having a substantial degree of homology as well as be able to bind selectively with varying types and sources of nucleic acid fragments having the complementary target sequence as part of its composition. Thus, the size or length of the oligonucleotide probe and the repetitive nature of or copy number for the complementary target sequence will meaningfully affect not only the specificity, but the sensitivity of the probe for detection purposes.

The technique employing an oligonucleotide probe for selective binding to a complementary target sequence is generally termed "hybridization". However, the development of hybridization based assays for the identification of specific genes and gene expression products has been severely limited to date because of major difficulties in: (a) isolating highly specific nucleic acid sequences for use as oligonucleotide probes; (b) developing assay formats that are sufficiently rapid and simple in order to identify even one complementary target sequence in a fluid mixture containing many varieties of different single-stranded oligonucleotides in admixture; and (c) devising non-radioactive detection systems that provide a desired level of sensitivity. Thus, several types of DNA (or RNA, or PNA) hybridization assay formats have come into prevalent use.

Four hybridization assay formats are commonly employed today. Each of these hybridization detection formats suffers from relatively poor sensitivity, although various target sequence amplification techniques (such as PCR) have also been developed to reduce the severity of this problem. The four most commonly used types of hybridization assay formats are: the Southern blot technique; the dot or spot blot technique; in-situ hybridization; and sandwich hybridization assays. As with the selection of an appropriate oligonucleotide probe, the choice of a hybridization assay format often rests upon the degree of specificity and sensitivity that is required for the particular analysis; and upon the factors of speed, reliability, and ease of performance and interpretation of the assay result—which varies markedly among the different assay formats.

In Southern blot assays, specimen DNA is isolated and purified prior to restriction endonuclease digestion; followed by separation of the digestion products by electrophoresis on an agarose gel, denaturation of the DNA in the gel, and transfer of the denatured DNA fragments to a solid matrix such as a nitrocellulose membrane. The DNA bound to the solid matrix is then hybridized in the presence of radioactively labeled DNA targets to establish homology between the probe and target DNA. Hybridization of the targets to the probes is detected by autoradiography and often requires several days or weeks of exposure. This format is thus often too lengthy and cumbersome for routine or large-scale analyses of many specimens.

The dot-blot procedure also requires that specimen DNA be isolated and purified before being denatured and applied to a suitable solid matrix (such as nitrocellulose). Hybridization to the matrix-bound DNA is then performed using probe-specific targets. The hybridization of target DNA to the probe DNA is detected either by autoradiography or by visual inspection using non-radioactive detection procedures. The spot-blot assay format is similar except that specimens or specimen lysates are directly applied to the solid matrix without prior extraction of their DNA. Although this assay format allows many different samples to be processed at one time, these assays are often limited to high background noise that complicates the interpretation of results and is also subject to lengthy time of processing for each sample to be evaluated.

The in-situ hybridization technique intends that the DNA or RNA in the cells of a fixed tissue section or fixed culture cell be hybridized to DNA probes directly on a microscope slide. The results are determined by microscopy if non-radioactive detection systems are used and by autoradiography if radioisotopes are employed for the targets.

This assay format can detect the presence of only a few copies of the target DNA sequence to be hybridized. The conventional in-situ hybridization assay is not suitable for screening large numbers of specimens due to the need to separate and remove extraneous cellular materials from the sample prior to addition of the labeled target.

Lastly, the sandwich hybridization assay requires that at least two different specific probes hybridize to the target DNA of interest, rather than just one probe alone. In this format, the first probe (the capture sequence) is bound to a solid support and is allowed to bind (capture) the specimen DNA A second probe (the signaling probe) with a sequence that is adjacent or close to the capture sequence on the target DNA molecule is then allowed to hybridize to the support-bound target DNA. This signaling probe can be labeled with either radioactive or non-radioactive labels; and the removal of non-specific cellular material in the first step of the procedure enhances the specificity of the hybridization assay by reducing the effects of contaminating tissue or debris.

More recently however, the value of using immobilized, spatially distinguishable, hybridization probes for concurrent analyses of multiple gene sequences has been recognized and resulted in the development of miniaturized hybridization assays using solid matrix assays [Southern, E.M., *Trends in Genetics* 12: 110–115 (1996)]. Thus, hybridization using said matrix arrays have been performed on glass surfaces [Maskos, U. and E.M. Southern, *Nuc. Acids. Res.* 20: 1679–1684 (1992); Guo et al., *Nuc. Acid. Res.* 22: 5456–5465 (1994)]; on microtiter plates [Kalakowski et al., *Anal. Chem.* 68: 1197–1200 (1996); Nikiforov et al., *Nuc. Acids Res.* 22: 4167–4175 (1994); Rasumussen et al., *Anal. Biochem.* 198: 138–142 (1991)]; on plastic sheets [Matson et. al. *Anal. Biochem.* 224: 110–116 (1995)]; on thin polymer gels [Khrapko et al., *J. DNA Seg. Map.* 1: 375–388 (1991)]; and using semiconductor devices [Eggers et al., *Bio Techniques* 17: 516–524 (1994); Kreiner, T, *Am. Lab.*: 39–43 (1996)]. In addition, the desire for using non-radioactive means for detection have caused a surge of interest in means for detection of hybridization on solid matrix supports which employ fluorescence [Kumke et. al., *Anal. Chem.* 67: 3945–3951 (1995); Piunno et. al., *Anal. Chim. Acta.* 288: 205–214 (1994)]; chemiluminescence [Ito et. al., *J. Neurosci. Methods* 59: 265–271 (1995); Nguyen et. al., *Biosen. Bioelectron.* 7: 487–493 (1995)]; evanescent wave technology [Graham et al., Biosen. Bioelectron. 7: 487–493 (1992); Strachan et. al., *Lett. App. Microbiol.* 21: 5–9 (1995); Watts et. al., *Anal. Chem.* 67: 4283–4289 (1995)]; confocal microscopy [Fodor et. al., Nature (London) 364: 555–556 (1993)]; light scattering [Stimpson et. al., *Proc. Natl. Acad. Sci. USA* 92: 6379–6383 (1995)]; electrochemistry [Milland et. al., *Anal. Chem.* 66: 2943–2948 (1994); Pandey et. al., *Anal. Chem.* 66: 1236–1241 (1994); Hashimoto et. al., *Anal. Chim. Acta.* 286: 219–224 (1994)]; and surface resonance phenomena [Yamaguchi et. al., *Anal. Chem.* 65: 1925–1927 (1993)].

Despite these recent innovations using probes immobilized on solid matrix arrays the major obstacles and limitations of hybridization methods generally continue to restrict and contain the currently available techniques and formats. These demands and limitations include a requirement for a large sample volume; an inability to perform multiple analyses concurrently in real time; a requirement for a relatively high concentration of target DNA (the complementary target sequence) in the fluid sample; an inability to detect multiple species concurrently; relatively slow kinetics for hybridization to occur between the target sequences and the immobilized probes within the assay format; and a dependence upon lengthy assays. Moreover, despite the use of new in-vitro amplification techniques such as the polymerase chain reaction procedure, the problems of assay sensitivity, lengthy times for analysis, the quantum of background signal noise, and the inability to detect more than one target nucleic acid sequence at a time remain as recurring handicaps and continuing obstacles for each of these techniques. It will be recognized and appreciated by persons working in this field today, therefore, that the development of a unique biosensor which overcomes and eliminates most, if not all, of these major limitations and procedural hindrances would be seen as a major advance and unforeseen improvement in this art.

SUMMARY OF THE INVENTION

The present invention has multiple aspects and formats. A first aspect provides an optical biosensor for selectively detecting an oligonucleotide specie in a fluid sample, said biosensor comprising:

a clad optical fiber strand of determinable configuration and dimensions which presents two strand end faces as discrete optic surfaces for introduction and conveyance of light energy;

an oligonucleotide in-situ hybridization zone comprising one specie of single-stranded oligonucleotide disposed as a deposit upon one of said strand end faces of said optical fiber strand, said deposit of single stranded oligonucleotide within said hybridization zone serving as a deployed, single specie, fixed probe suitable for selective in-situ hybridization on-demand with a mobile complementary oligonucleotide target specie, (a) wherein such complementary oligonucleotide target specie as is hybridized in-situ ultimately bears a joined identifying label comprising at least one light energy absorbing dye of known spectral characteristic, and (b) wherein the resulting, specie specific, in-situ hybridized oligonucleotide reaction product formed by a complementary oligonucleotide target specie with said fixed probe at said hybridization zone is optically detectable via the spectral characteristics of said joined identifying label concomitantly disposed at said strand end face surface.

A second aspect defines an optical biosensor for selectively detecting at least one oligonucleotide specie in a fluid sample, said biosensor comprising:

a bundled array comprising a plurality of individually clad, fiber optic strands disposed co-axially along their lengths and having two discrete array ends each of which is formed of multiple strand end faces, said bundled array being of determinable configuration and dimensions and said two discrete array ends presenting two optic array surfaces for introduction and conveyance of light energy; and at least one oligonucleotide in-situ hybridization zone comprising a plurality of single stranded oligonucleotide species disposed as individual specie deposits in aligned organization at differing spatial positions on one zone of said optic array end surface of said bundled array, the differing spatial positionings for each deposit of single stranded oligonucleotide specie in aligned organization within said hybridization zone serving as deployed, single specie, multiple fixed probes suitable for selective insitu hybridization on-demand with its mobile complementary oligonucleotide target specie, (a) wherein such complementary oligonucleotide target specie as is hybridized in-situ ultimately bears a joined identifying label comprising at least one light energy absorbing dye of known spectral characteristics, and (b) wherein the resulting, specie specific, in-situ hybridized oligonucleotide reaction products formed by a complementary oligonucleotide target specie with said multiple fixed probes at said differing spatial positions within said hybridization zone are optically detectable via the spectral characteristics of said identifying label concomitantly disposed at said differing spatial positions.

A third aspect of the present invention provides an optical biosensor for selectively detecting a plurality of individual oligonucleotide species concurrently in a fluid sample containing a mixture of different oligonucleotide species, said biosensor comprising:

a preformed, unitary fiber optic array comprising a plurality of individually clad, fiber optic strands disposed coaxially along their lengths and having two discrete optic array ends each of which is formed of multiple strand end faces, said preformed unitary fiber optic array being of determinable configuration and dimensions and said two discrete optic array ends presenting two discrete optic array surfaces for introduction and conveyance of light energy; and at least one oligonucleotide in-situ hybridization zone comprising a plurality of single-stranded oligonucleotide species disposed as individual specie deposits in aligned organization upon multiple strand end faces at differing spatial positions on one of said discrete optic fiber array surfaces of said unitary fiber optic array, the differing spatial positionings for each deposit of singlestranded oligonucleotide specie in aligned organization within said in-situ hybridization zone serving as a collective of deployed, specie specific, fixed probes suitable for selective in-situ hybridization onemand with its mobile complementary oligonucleotide target specie in a fluid mixture containing alternative mobile complementary target species, (a) wherein such hybridized complementary oligonucleotide target species as are hybridized in-situ each ultimately bears a joined identifying label comprising at least one light energy absorbing dye of known spectral characteristics, and (b) wherein the resulting, species specific, in-situ hybridized oligonucleotide reaction product formed by a complementary oligonucleotide target specie with its collective of multiple fixed probes at said differing spatial positions within said hybridization zone is optically detectable via the spectral characteristics of said joined identifying label concomitantly disposed at said differing spatial positions, each alternative in-situ hybridized oligonucleotide reaction product formed being concurrently optically detectable via the spectral characteristics of each joined identifying label at differing spatial positions within said hybridization zone.

BRIEF DESCRIPTION OF THE FIGURES

The present invention may be more easily understood and better appreciated when taken in conjunction with the accompanying drawing, in which:

FIG. 1 is an overhead view of an individually clad, optical fiber strand;

FIGS. 2A and 2B are views of the proximal and distal surfaces of the fiber optical strand of FIG. 1;

FIGS. 3A and 3B are alternative constructions of the optical end surface for the optical fiber strand of FIG. 1;

FIG. 4 is an overhead view of a bundled array of single core, optical fiber strands;

FIGS. 5A and 5B are views of the distal and proximal end surfaces for the bundle of fibers of FIG. 4;

FIG. 6 is an overhead view of a preformed, unitary fiber optic array using the optical fiber strand of FIG. 1;

FIG. 7 is a view of the intended distal array end surface of the unitary fiber optic array of FIG. 6;

FIG. 8 is a view of the intended proximal array end surface of the unitary fiber optic array of FIG. 6;

FIG. 9 is a frontal view of an illumination source able to provide light energy at precise spatial positions concurrently;

FIGS. 10–15 illustrate the manipulative steps performed during the disposition of oligonucleotide probes at precise spatial positions on the distal array end surface of FIG. 8.

FIG. 16 is a schematic diagram of the apparatus comprising the biosensor;

FIG. 17 is a schematic diagram of a fiber optic biosensor detection apparatus and system;

FIGS. 18A and 18B are white light and background fluorescent images viewed through the proximal end of the biosensor apparatus;

FIG. 19 is a graph showing the background-subtracted mean fluorescence intensities obtained with fixed IL4 probes on the distal end of the biosensor, FIG. 20 is a graph showing the plot of background-subtracted mean fluorescence as a function of time using a sensor having a β-glo probe and a 1.0 µM β-glo target solution;

FIG. 21 is a graph showing the plot of background-subtracted mean fluorescence as a function of time using a sensor having a β-glo probe and an 0.1 µM β-glo target solution;

FIGS. 22A–22F are fluorescent images from a biosensor apparatus after immersion in a IL2 target, a IL4 target, an IL6 target, a β-glo target, an IFNG target, a IL4 and IFNG and β-glo targets;

FIG. 23 is a graph illustrating the background-subtracted mean fluorescence signals as a function of the probe/target pair of FIG. 22;

FIG. 24 is a graph showing the plot of hybridization competition between labeled and unlabeled formats of the same target nucleic acid sequence;

FIG. 25 is a graph showing the fluorescence intensity of the poly(dA) matrix upon repeated hybridization to and dehybridization from a poly(dT)-FITC target;

FIG. 26 is a graph showing the fluorescence intensity of a poly(dA)/acrylamide biosensor to varying concentrations of poly(dT)-FITC;

FIG. 27 is a graph showing the calibration curve of the data of FIG. 25;

FIG. 28 is a graph showing the calibration curve of a poly(dA) matrix biosensor after in-situ hybridization with a poly(dT)-biotin target;

FIG. 29 is a graph showing the melting curves of a DNA biosensor after hybridization to a Δ target at 28° C.;

FIGS. 30A and 30B are fluorescent images from the DNA biosensor apparatus after in-situ hybridization with a Δ-FITC target at 28° C. and 50° C. respectively;

FIG. 31 is a graph showing the fluorescence intensity over time for in-situ hybridization of a 196 nM Δ target to a H-ras wt./H-ras Δ matrix biosensor;

FIG. 32 is a graph showing the calibration of a DNA biosensor to a Δ-FITC target at 54° C.; and FIG. 33 is a fluorescence image from a DNA biosensor apparatus after a 20 minute hybridization time to a biotinylated Δ PCR amplicon at 54° C., followed by a 5 minute labeling reaction with streptavidin-FITC.

DETAILED DESCRIPTION OF THE INVENTION

The present invention is a fiber optic biosensor comprising at least one fiber optic strand; can comprise a bundled array of single core fibers joined together; and preferably comprises a preformed, unitary array of fibers—these biosensor types having at least one and desirably several, oligonucleotide probes immobilized at individual and differing spatial positions on the distal end surface. The immobilized oligonucleotide probe(s) do not bear any identifying label of any kind. Rather, when the distal strand end surface or, alternatively, the distal array end surface supporting the immobilized probes are placed into reactive contact with a fluid sample containing at least one complementary target oligonucleotide segment bearing a joined identifying label, an in-situ hybridization will occur; and the reaction product of the in-situ hybridization (formed by a complementary oligonucleotide target collectively with the immobilized probe at each of the differing spatial positions on the distal end surface) can be detected and monitored by observing the fluorescence or reflected color of the joined identifying label that accompanied or is the consequence of hybridization at that specific spatial position. Equally important, because the hybridization is specific between the oligonucleotide base sequence of the spatially immobilized probe with a complementary target base sequence, the detection of fluorescent or reflected light energy from the joined label at a predetermined spatial position on the distal end surface will demonstrate and evidence the occurrence of a specific and selective in-situ hybridization.

A number of different major advantages and unique capabilities are thus provided by the biosensor comprising the present invention. Among these advantages and capabilities are the following.

1. The present invention provides a biosensor which offers a choice of formats using a single optical fiber strand; or a bundled array of single core fibers joined together; or, alternatively, a plurality of optical fiber strands disposed co-axially along their lengths as a preformed unitary fiber optic array. The single optical strand format will provide one oligonucleotide hybridization zone and a single specie fixed probe suitable for selective in-situ hybridization with one mobile complementary oliognucleotide target specie. The bundled array of fibers format provides multiple hybridization zones and multiple single specie fixed probes for selective in-situ hybridization with one or a plurality of different mobile complementary oligonucleotide species. The alternative unitary fiber optic array format provides collectives of multiple and different fixed sets of specie-specific probes, each set of fixed probes being collectively suitable for selective in-situ hybridization with a different mobile complementary oligonucleotide target specie. The unitary fiber optic array format and the bundled array of fibers format are thus able to detect multiple and diverse types of mobile oligonucleotide target species simultaneously or concurrently in one sample and a single test; in comparison, single optical fiber strand format is limited to the detection of a single oligonucleotide target specie per sample and test.

2. The present invention, in all formats, is able to detect one specific target nucleic acid segment in a fluid mixture of different oligonucleotide fragments; and, in two formats, is able to detect a plurality of different complementary target oligonucleotide species in a single fluid sample containing a mixture of many different nucleic acid sequence fragments. The specificity of the in-situ hybridization reaction depends primarily upon the choice of oligonucleotide probe employed. Thus, when probes are chosen which have a known base sequence and having a recognized or specified binding capability, the hybridization is highly selective and specific for a single complementary nucleic acid target sequence; and only selective binding to that one complementary species will occur despite the presence of other oligonucleotides in the fluid sample. Similarly, multiple and different in-situ hybridization reactions can concurrently occur at different spatial positions on the distal array end surface using a variety of alternative fixed probes. Each fixed probe is species specific; is fixed at a predetermined spatial position on the distal end surface; and will hybridize in-situ on-demand with its intended complementary target specie.

3. The present invention provides a biosensor which is extraordinarily rapid in providing evaluations and results based on in-situ hybridization reactions. Typically, the biosensor will provide optical detection of a labeled complementary target specie in a fluid sample in less than ten (10) minutes time; and depending on the chosen components of the detection system, may provide optical detection of multiple target species concurrently or simultaneously within the same time duration, approximately ten minutes or less. The present invention thus provides a speed of detection which is unmatched by any previously known format or conventional technique.

4. The present invention provides an extremely high level of sensitivity for in-situ hybridization reaction. As the experimental data provided hereinafter reveals, even a simple embodiment of the biosensor and its supporting apparatus can optically detect 10 nM of a target oligonucleotide segment via the spectral characteristics of a joined identifying label. The apparatus and method of optical detection yields very little background signal as noise; and it is expected that as little as 0.01–0.1 nM will be detectable under optimum operating conditions. Accordingly, the traditional requirement for high concentrations of DNA (or RNA, or PNA) test sample in order that an accurate and reliable measurement be made is no longer necessary or required. Also, the absolute amounts of DNA (or RNA, or PNA) needed for detection are small due to the extremely small size of the sensor.

5. The present invention will provide high specificity of in-situ hybridization reactions in a fluid sample when used at ambient room temperatures generally, or at elevated temperatures. No special or unique environmental considerations or demands are necessary in order to use the present invention; to the contrary, the sole requirement is that the distal end surface bearing the specie-specific fixed probes be placed in reactive contact with a fluid sample suspected of carrying the complementary target base sequence.

6. The present invention requires only a very small fluid sample volume in order for optical determinations to be made and accurate results to be obtained. If necessary, a few nanoliters of fluid may be employed for detection purposes. It is generally desirable, however, that a 1–2 microliter volume or greater be employed as the fluid sample. This low volume feature for the fluid sample may be maintained so long as there is sufficient liquid volume to cover the distal end surface effectively such that the fixed probe(s) immobilized on the distal surface may come into reactive contact with the contents of the fluid sample itself. If this minimal requirement is met and satisfied by the user, the true volume of the fluid sample is irrelevant and inconsequential.

7. The present invention also allows the user the ability to monitor the hybridization process over time in-situ without physical separation of the apparatus from the fluid sample undergoing evaluation. Thus, assuming the user employs a very rapid reaction time for analysis (less than 10 minutes), continuous observation and optical detection of the ongoing hybridization process over the 10 minutes can be made for one or for all of the differing spatial positions for the fixed probes immobilized on the distal end surface. Thus as hybridization occurs at each fixed probe location on the end surface, the presence of a bound label joined directly or indirectly to the complementary target specie will be detected via the spectral characteristics of the light energy absorbing dye employed as an identifying label. The user may thus monitor the ongoing reaction in real time as it actually proceeds in-situ; and may determine even more quickly whether or not the complementary target specie does in fact exist within that fluid sample.

8. The biosensor of the present invention allows the user not only to detect rapidly the presence of the complementary target base segment in a fluid sample, but also permits the user to quantify in proportional degree the concentration of the complementary target specie actually present in the fluid sample volume. A semiluantitative estimate is based on a calibrated detection of the signal intensity emanating from the fixed probes undergoing in-situ hybridization with the fluid sample. In addition, a competitive assay in which a fixed amount of added labeled target specie is displaced proportionately by an unknown quantity of unlabeled target in a test sample will also provide quantitative results. A quantitative estimate which is both reliable and reproducible is rarely otherwise available without much more rigorous experiments and analytical test conditions.

For easier comprehension and a better appreciation of the features and attributes of the present invention, the detailed disclosure herein will be presented in separate sections seriatim. The order of presentation will be: a detailed description of the unitary fiber optic array comprising the biosensor; the DNA (or RNA, or PNA) oligonucleotide(s) which may be employed as probes; a preferred means for immobilizing the oligonucleotide probes at differing spatial positions on the distal array end surface; the supporting apparatus desirably employed with the biosensor for detecting in-situ hybridization reactions on-demand; a description of complementary nucleic acid segments as target species; the manner of identifying the resulting in-situ hybridized reaction product; and a series of experiments and empirical results demonstrating some of the major advantages and unusual benefits provided by the present invention. Each of these will be described in detail below.

Also, since the present invention is definable in multiple formats and may be employed in different modes for a variety of divergent purposes and applications, the subject matter as a whole which is the present invention will be presented and described individually as component parts and then collectively as assemblies in order that the prospective user may more quickly recognize and appreciate their major differences and distinctions in comparison to the conventionally known systems.

I. The Organization And Construction Of The Biosensor

The unique biosensor may be prepared in three different formats. The simplest format employs a single optical fiber strand; and presents a single oligonucleotide in-situ hybridization zone disposed on the distal end surface comprising a single specie of single-stranded DNA (or RNA, or PNA) disposed as a fixed probe for selective hybridization with one mobile complementary target specie. A more elaborate format is the bundled array of single core fibers joined together. This format type presents an in-situ hybridization zone; and allows the user a choice of employing either a single specie or multiple species of DNA (or RNA or PNA) as fixed probes for selective in-situ hybridization. The alternative and most sophisticated format employs: a preformed, unitary fiber optic array comprised of a plurality of individually clad fiber optical strands disposed co-axially along their lengths; and at least one oligonucleotide in-situ hybridization zone comprising not less than one specie of single-stranded DNA (or RNA, or PNA) disposed as a plurality of individual deposits in aligned organization upon multiple fiber optical strand end faces at differing spatial positions and which serve as a collective of multiple fixed probes for specie selective in-situ hybridization on-demand. Each format will be described in detail.

A. The Format Choices

The individually clad, optical fiber strand

A typical optical fiber strand is illustrated by FIGS. 1 and 2A and 2B. As seen therein, an individual optical fiber strand 10 is comprised of a single optical fiber 12 having a rod-like shaft 14 and two fiber ends 16, 18, each of which provides a substantially planar end surface. The intended distal surface 20 at the fiber end 16 is illustrated by FIG. 2A, while the intended proximal surface 22 at the fiber end 18 is illustrated within FIG. 2B. It will be recognized and appreciated that the terms "proximal" and "distal" are relative and interchangeable until the strand is ultimately positioned in an apparatus. The optical fiber 12 is composed typically of glass or plastic; and is a flexible rod able to convey light energy introduced at either of its ends 16 and 18. Such optical fibers 12 are conventionally known and commercially available. Alternatively, the user may himself prepare individual optical fibers in accordance with the practices and techniques reported in the scientific and industrial literature. Accordingly, the optical fiber 12 is deemed to be conventionally known and available as such.

It will be appreciated that FIGS. 1–2 are illustrations in which the features have been purposely magnified and exaggerated beyond their normal scale in order to provide both clarity and extreme detail. Typically, the conventional optical fiber has a cross section diameter of 5–500 micrometers; and is routinely employed in lengths ranging between meters (in the laboratory) to kilometers (in field telecommunications). Moreover, although the optical fiber 12 is illustrated via FIGS. 1–2 as a cylindrical extended rod having substantially circular proximal and distal end surfaces, there is no requirement or demand that this specific configuration be maintained. To the contrary, the optical fiber may be polygonal or asymmetrically shaped along its length; provided with special patterns and shapes at the proximal and/or distal faces; and need not present an end surface which is substantially planar. Nevertheless, for best efforts, it is presently believed that the substantially cylindrical rod-like optical fiber having planar end surfaces is most desirable.

Each optical fiber 12 is desirably, but not necessarily, individually clad axially along its length by cladding 26. This cladding 26 is composed of any material with a lower refractive index than the fiber core and prevents the transmission of light energy photons from the optical fiber 12 to the external environment. The cladding material 26 may thus be composed of a variety of radically different chemical formulations including various glasses, silicones, plastics, platings, and shielding matter of diverse chemical composition and formulation. The manner in which the optical fiber 12 is clad is also inconsequential and of no importance to the present invention. Many methods of deposition, extrusion, painting and covering are scientifically known and industrially available; and any of these conventionally known processes may be chosen to meet the requirements and convenience of the user. Moreover, the quantity of cladding employed need only be that minimal amount which effectively prevents light energy conveyed by the optical fiber 12 from escaping into the ambient environment. It will be recognized and appreciated therefore, that the depth of cladding 26 as appears within FIGS. 1 and 2 respectively is greatly exaggerated and purposely thickened in appearance in order to show the general relationship; and is without scale or precise ratios between the cladding 26 and the optical fiber 12.

It will also be recognized that the configuration of the cladding 26 as shown by FIGS. 1 and 2 has been shaped as a circular coating to illustrate a preferred embodiment only. For reasons as will become clear subsequently, it is desirable that the cladding 26 take form in regular geometric form such as a round or circular shape. The illustrated configuration, however, is merely a preferred embodiment of the cladding 26 as it extends co-axially along the length of the optical fiber 12. For purposes of added clarity also, FIG. 1 reveals the individually clad, optical fiber strand 10 is partial cross-section to demonstrate the relationship between the optical fiber core 12 and the cladding 26 which is coextensive along its length.

The user also has a variety of choices at his discretion regarding the configuration of the "distal" end 16 of the optical fiber 12 as shown by FIGS. 3A and 3B; however, both ends of the strand must be the same—i.e., if the "distal" end is cylindrical then the "proximal" end must be also. As seen in FIG. 3A, the "distal" end 16 is substantially cylindrical in shape and desirably presents a surface 20 which is substantially planar and smooth. A possible, but less desirable, alternative is shown by FIG. 3B, in which the distal end 30, nevertheless provides a very different end surface for the optical fiber 12. The surface 32 includes a depression or well 34 which extends into the substance of the optical fiber 12 at a depth typically of several micrometers. Although the well 34 appears substantially circular within FIG. 3B, oval or other rotund configured depressions may also be employed as fits the needs or convenience of the use. Similarly, the void volume of the well 34 from its greatest depth to the proximal surface 32 may also be varied.

It will be recognized and appreciated as well that the range and variety of dimensional and configurational divergence for the strand end is limited only by the user's ability to subsequently dispose and immobilize an oligonucleotide of known composition/formulation of controlled thickness on the intended distal surface of the optical fiber 12. In some embodiments, a greater depth of deposit on the surface of the distal end surface may be highly desirable; nevertheless, for most general assay purposes, both quantitative and qualitative, the intended distal surface illustrated within FIG. 3A as a substantially planar and smooth surface is deemed to be most suitable and desirable. For general construction of the single strand sensor and for most purposes and applications of the improved optical detecting system and procedures described hereinafter, it is desirable to employ the individually clad, fiber optical strand illustrated by FIGS. 1, 2A, 2B in preference to a bare, unsheathed strand. Clearly, the optical fiber strand is unable to transmit light energy photons to any other entity due to the cladding material 26 which forms a sheath. This sheath, having a refractory index less than the strand core, also prevents loss of light energy photons into the general environment. Accordingly, the potential for photon loss, distortion, or other optical error is minimized and reduced. For these reasons, the individually clad optical fiber mode of construction is preferable to the use of bare optical fiber strands in order to achieve greater precision and accuracy.

The bundled array of single core fibers

It will be noted that the bundling of individual single core fibers into an organized array can be made either before or after one oligonucleotide specie has been deposited and immobilized on the distal end surface of each optical fiber strand forming the bundled array of fibers. A detailed and empirically evaluated bundled array of fibers prepared in advance and used herein as a biosensor is presented by the data of Experimental Series A comprising Experiments 1–5 respectively.

For illustrative purposes and ease of understanding, however, the detailed description in this section will limit itself to a bundled array of fibers which do not yet have any oligonucleotide specie immobilized onto their individual strand end faces. In addition, the number of individual, single core, optical fibers employed in a bundled array format has been intentionally limited to only three strands. It will be recognized and appreciated, however, any small quantity of single core optical fiber strands ranging in number from not less than 2 to about 20 fibers can be combined together as a single discrete bundle, the exact number of single core strands being bundled into an array depending greatly upon the size of the core strands.

The bundling of individual, single core, optical fiber strands into an organized array is a conventionally known technique and is well established in this field. A number of different bundling formats are well known which combine prepared individual single strand sensors as an integrated bundle for a specific purpose. Merely examplifying the conventionally known range of articles using the bundled array of fibers format are European Patent Application 88105676.6; and U.S. Pat. Nos. 5,047,627 and 4,999,306, as well as the references cited within each of these.

Accordingly, a typical bundled array of single core optical fibers is illustrated by FIGS. 4 and 5 respectively. As seen therein, the bundled array 40 formed of single core fibers appears as a substantially triangular-shaped integrated article having a distal end face 42 and a proximal end face 44; and is comprised of three different and distinct, single core, optical fiber strands 50, 60, and 70 which are disposed co-axially along their lengths to form the integral bundle. Each of the individual strands 50, 60, and 70 is a single optical fiber strand having a distal strand end face 52, 62, 72 and a proximal strand end face 54, 64, 74. Also, each strand has a single optical core 56,66, and 76 which is individually covered and surrounded by cladding material 58, 68, and 78.

By way of example, as shown in FIGS. 4 and 5, three single core fibers 50, 60, 70 are shown joined together as a configured bundle using epoxy adhesives which are optically dense and using such additional cladding material as is necessary as a bulk filler to form an integral fiber bundle 40 configured in substantially triangular form. Note that each optical fiber strand in the bundled array 40 has been spatially oriented and intentionally placed into a triangular configuration such that fiber strand 50 lies at the apex while fiber strands 60 and 70 lie at the base of the shaped bundle. Once placed and immobilized into this triangular organizational format, the spatial positioning for each of the three single core fibers 50, 60, and 70 within the bundled array 40 is always maintained.

Furthermore, FIG. 5A shows that the distal ends 52, 62, 72 of each respective single core strand 50, 60 and 70 each individually extends for a short distance (typically several centimeters) beyond the protective sheath 41. This is a desirable feature which facilitates the subsequent immobilization of one oligonucleotide specie to the distal strand end of each face 52, 62, and 72 respectively. In comparison, FIG. 5B shows that the proximal end face 44 of the bundled array 40 is coextensive with the proximal strand end faces 54, 64, and 74 of the single core fibers 50, 60 and 70 respectively. The unitary array A typical preformed fiber optic array, its organization and construction, and its component parts are illustrated by FIGS. 6–8 respectively. Each discrete, unitary fiber optic array is a preformed composite comprised of a plurality of individually clad, fiber optical strands disposed coaxially along their lengths. The smallest common repeating unit within the preformed array is thus a single optical fiber strand. The manner in which these optical fiber strands are prepared and the manner in which these prepared optical strands are joined collectively into an organized optic array are conventionally known, but is fundamental to a proper understanding and use of the alternative format.

It is recognized also that the unitary array of optical fibers has been used previously as a major component in other inventions and is described in earlier issued patents. Such usage is exemplified by U.S. Pat. Nos. 5,244,636; 5,244,813; 5,250,264; and 5,298,741; the texts of which are individually expressly incorporated by reference herein.

The unitary fiber optic array 100 appears in exaggerated, highly simplified views without regard to scale within FIG. 6. The preformed array is composed of a plurality of individually clad, fiber optical strands which collectively lie co-axially along their respective lengths as the discrete, unitary optic array 104 of fixed and determinable configuration and dimensions. The optic array 104 has a unitary, rod-like collective body 106 and intended distal and proximal collective ends 108, 110 formed of multiple strand end faces. The intended distal collective end 108 provides a substantially planar and smooth optic array surface 114 The topographical surface 116 is the result of fusing the clad of each fiber optical strand 102 collectively with a fiber material 118 such that the fusion is drawn and appears as a discrete, unitary array. In this manner, the exterior surface 116 of the collective array body 106 may be configured and dimensioned as an assembly in an acceptable manner and useful manner. It will be recognized and appreciated also that a substantially cylindrical configuration and topography is maintained and presented by the unitary imaging fiber optic array 100 merely as one preferred embodiment. Any other regular or irregular configuration and design may be achieved and employed to satisfy the individual user's needs or desires.

For purposes of clarity and ease of understanding FIGS. 7 and 8 present a very limited and greatly reduced number of individually clad, fiber optical strands 102 present within the preformed optical array 104. A total of only 120 individually clad, fiber optical strands are seen to comprise the optical array 104 in greatly magnified and scale-exaggerated views. Moreover, the relationship of the optical array surface 112 (the intended distal end) with respect to the other optical array surface 114 (the intended proximal end) becomes simplified and more-readily appreciated when using this limited number of 120 optical fiber strands. In practice and reality, however, it is estimated that typically there are 2000–3000 optical fiber strands in a conventional array of 200 μM diameter. Thus the true total number of individually clad, fiber optic strands forming the unitary imaging fiber optic array will typically be in the thousands and vary substantially with the cross-sectional diameter of each optical fiber and the thickness of the cladding material employed when constructing the optical fiber strands themselves.

The construction, coherent organization, and positional alignment within a typical fiber optic unitary array is revealed by FIGS. 6–8. For descriptive purposes only, each of the individually clad, optical fiber strands is presumed to be linearly straight in position and has been arbitrarily assigned an identifying number S1–S120 as shown via FIGS. 7 and 8. The intended distal optic array end surface 112 of FIG. 7 shows that each of the individual optical fiber strands S1–S120 can be identified and distinguished from its adjacently disposed neighbor as well as from any other optical fiber strand within the preformed array 104 by a set of spatial positioning coordinate numbers for the strand end faces. The intended distal optical array surface 112 may be arbitrarily divided into two axial directions as is illustrated by FIG. 7. The exact location of the S1 strand is thus identifiable by the numerical coordinates "XII D" showing the strand end face. Similarly, the exact spatial positioning and strand end face of the S72 fiber is designated as "VIM." In this manner, the individual spatial position and strand end faces for each optical fiber strand S1–S120 is thus completely locatable and identifiable using the coordinate numeral labeling system.

The other optic array end surface 114 (the intended proximal end surface) allows for a similar mode of identification (presuming straight linear alignment of strands) by spatial positioning of each individual optical strand—again as a result of using dual-axis numerical coordinates as seen in FIG. 8. Accordingly, fiber end strand end face S1 is located at numerical position "12d", and fiber S72 is identifiable, locatable, and distinguishable from all other fibers at the optic array surface by its individual numerical coordinates "6m". In this manner, the precise and exact position of each individually clad optical fiber strand and strand end faces on each of the discrete optic array surfaces 112, 114 can be located, identified, and specified via a series of two different numerical coordinates. The intended distal and proximal optic array surfaces are thus completely identifiable and distinguishable as per individual fiber optical strand 102 despite its presence in the preformed collective body 106 of the unitary fiber optical array 100.

It will be appreciated also that the overall organization of the individually clad, optical fiber strands 102 within the unitary array 100 of FIGS. 6–8 is as aligned, parallel, strands which maintain their relative organizational positioning in a coherent, consistently aligned manner over the entire length of the collective body 106. This is deemed to be the most desirable and most easily constructable organization scheme for the preformed optical fiber array of the present invention.

Although this highly organized, coherent, and rigidly aligned collective construction is deemed to be most desirable, this high degree of organizational alignment is not an absolute requirement for each and every embodiment using an unitary optical array. Alternative manufacturing practices allow for a more random disposition of the individually clad, optical fiber strands disposed co-axially along their lengths. Although less desirable, a partially random disposition and a completely random alignment of the optical fiber will also result in a unitary collective body of optical fibers and in proximal and distal collective ends which provide two discrete optical array surfaces. It will be recognized therefore that while the individually clad, optical fiber strands may lie adjacent one another at one end, they may deviate and meander through the length of the array such that their position relative to one another may vary substantially in part or in whole—thereby creating semiocoherent or incoherent positional alignments which vary in the randomess of their organizational construction. There is no requirement that the positioning of the intended proximal end of one strand be aligned and/or identical with the positioning of the intended distal end within the unitary optic array.

The entirety of the construction for the unitary optical fiber array (whether uniformly coherent, semi-random, or completely randomly organized) provides a means of introducing light energy photos of any determinable wavelength at one optic array surface with the knowledge that the light energy will exit at the other optic array surface. Therefore, by using the preferred completely coherent and rigidly maintained parallel alignment of strands illustrated by FIGS. 7 and 8 (the intended distal and proximal optic array end surfaces respectively) of a unitary fiber optic array, the user may introduce light energy to a portion or all of the optic array end surface 114 and have accurate knowledge and confidence that the light energy would be conveyed by the fiber strands and exit from the other optic array end surface 112. Conversely, were light energy introduced to the optic array end surface 112, the light energy would be conveyed by the optical fibers of the array and will exit from the other optic array end surface 114.

In addition, the topography of the unitary optic array end surfaces 112 and 114 will vary with the nature of the end faces for the individual optical fibers strands comprising the array. Thus, if the optical fiber strand end faces conform to that illustrated by FIG. 3A, then the array end surface will present a substantially planar and smooth topography. Alternatively, however, if the optical fiber end faces forming the array are examplified by FIG. 3B; then the unitary array end surface will appear as a collective of wells or depressions, each well extending into the collective substance of the array end surface at a set depth (typically of a few micrometers). The topography of the unitary array end would then present a pitted and crater-like surface for the immobilization of oliognucleotides as fixed probes.

It will also be recognized that the user may chose to introduce light energy to only a specific spatial location on the optic array end surface 114—for example, only to fibers S1, S7 and S8—and have accurate knowledge and confidence that the light energy would be conveyed only by those three optical fiber strands and exit from numerical positions "XIID", "XIC", and "XID" alone on the optic array end surface 112. No other light energy would appear from any other spatial position from the optic array surface 112. Similarly, were light energy of specific wavelength introduced at the optic array surface 112 via fibers S107, S108, and S115, respectively, the use can accurately predict and identify that the light energy will be conveyed by only these three optical fibers; and will exit only at the optic array surface 114 of numerical coordinate position numbers 2c, 2d, and 1d respectively and from no other spatial positions on this optic array surface. In this manner, not only does one have knowledge of the individual spatial positioning of each optical fiber strand in the preformed array but also one has the ability to identify and precisely locate light energy photons emerging from individual optical fiber strands within the whole of the optic array surface in a practical and reliable mode.

Accordingly, the critical and essential requirements of any optical fiber array construction allows and demands the capability for precise spatial positional introduction and conveyance of light energy via different fiber optical strands within the collective body of the preformed, unitary fiber optical array. This capability to introduce light energy photons at precise spatial positions at one optic array of a unitary array; to convey the introduced light energy along the length of only a few fiber optical strands; and to control the exit of the conveyed light energy at a second, precisely known, spatial position on the other optic array surface of the unitary array is a hallmark of the singular fiber optic sensor presented herein.

B. Oligonucleotides Immobilized As One Or As Multiple Fixed Probes

The construction of the biosensor intends that at least one specie of single-stranded DNA, or RNA, or PNA, fragment be deployed and immobilized on the distal end surface of a single optical fiber strand; or on the distal end surface of at least one single core strand comprising an organized bundled array of optical fibers; or on the distal array end surface of a unitary array at differing spatial positions—and thus serve as one or more deployed fixed probes suitable for selective in-situ hybridization on-demand. Each specie of DNA (or RNA, or PNA) fragments is disposed as an individual deposit on at least one strand end face or as multiple independent deposits in aligned organization on multiple strand end faces at one or at many different spatial positions on the distal optic end surface. Each oligonucleotide specie deposit on an optical fiber strand end face, therefore, serves as one fixed probe immobilized at a predetermined spatial position; and in each of the array formats, the multiple fixed probes serve collectively as many singular and different reaction zones acting repetitiously and in common for in-situ hybridization with a mobile complementary nucleic acid target (directly or indirectly bearing a joined identifying label).

The nature of the oligonucleotide fragiment

The oligonucleotide sequence chosen for use as a probe may be obtained from any source; prepared or purified in any manner; vary in size or length without meaningful limit; and be used as a genetic tool for any research purpose, for a diagnostic goal or therapeutic application, or for any other result involving genetic manipulation. The chosen nucleic acid sequence may be DNA, or RNA, or a peptide nucleic acid (PNA) in composition; may be endogenously or exogenously derived; may be naturally occurring or synthetically prepared; may be composed of a minimum number of nucleic acid bases; or be composed of many thousands of nucleoti des in sequence. For example, the user may thus employ genomic or chromosomal DNA, plasmid DNA, and/or a cloned or replicated DNA which is representative of a marker or is unique for a virus, a bacteria, a particular cell type, or a cytoplasmic or nuclear zone within a cell. Similarly, the oligonucleotide or peptide nucleic acid fragment utilized may represent or comprise RNA in its many forms (such as messenger or transfer, or mitochondrial RNA) as it exists in nature or is synthetically produced. All of these diverse origins and sources of nucleic acid sequences are conventionally known; and many techniques for their individual preparation, isolation, and purification as single-stranded nucleic acid chains of known composition, sequence, and specific binding capabilities are available in the published literature today.

Regardless of the particulars regarding the nucleic acid sequence or fragment chosen for use as an oligonucleotide probe, two essential requirements must be met and satisfied in every instance. First, the nucleic acid segment should be of known composition and sequence order, and thus bind selectively and specifically with a particular complementary target sequence primarily, if not exclusively. The degree of selectivity and hybridization for the oligonucleotide probe will thus vary with the specificity of its nucleic acid sequence and the degree of homology permitted among different and competing complementary target species. Thus, the more controlled the nucleic acid sequence of the probe, the more selective and specific the binding with one complementary target specie. Second, the oligonucleotide probe must bind with its intended target at each and every instance and occasion where the complementary target species is presented for reactive contact. Thus, although the complementary target sequence may exist in single or low copy number and/or be encased in a larger-sized fragment containing non-cmplementary sequences, the oligonucleotide probe should nevertheless bind to the target portion of these larger mobile fragments when they come into reactive contact with the probe. Such binding capacity provides both specificity and sensitivity for the biosensor as a whole.

C. Oligonucleotide Probe Immobilization

When depositing the individual DNA or RNA oligonucleotide specie to be used as a probe on the end surface of a single optical fiber strand or at precisely spatially positioned locations on one optical array end surface, it is necessary that the oligonucleotide(s) remain immobilized at the single or the different spatial positions assigned to each of them individually without migrating towards any other position. Multiple methods of oligonucleotide probe deposition and immobilization are conventionally known and are suitable for use in making an embodiment of the present invention. Thus, one may prepare a specific formulation comprising one specie of DNA (or RNA, or PNA) bases in sequence and dispose the formulation at a specific spatial position and location on the optic end surface.

Among the conventional practices of deposition a variety of generally applicable polymerization processes are known, including thermal techniques, ionization methods, plasma methods, and electroinitiation procedures. These different methodologies are exemplified by the following publications, the text of each being expressly incorporated by reference herein. Thermal methods: Graham et al., *J. Org. Chem.* 44: 907 (1979); Stickler and Meyerhoff, *Makromal. Chem.* 179: 2729 (1978); and Brand et. al., *Makromol. Chem.* 181: 913 (1980). Ionization methods: A. Chapiro, *Radiation Chemistry of Polymer Systems* Chapter IV, Wiley-Intersciences, Inc., New York, 1962; J. E. Wilson, *Radiation Chemistry of Monomers, Polymers, and Plastics*, chapters 1–5, Marcel Dekker, New York, 1974. Plasma methods: Yasuda, W. and T. S. Hsu, *J. Polym. Sci. Polym. Chem. Ed.* 15: 81 (1977); Tibbett et al., *Macromolecules* 10: 674 (1977). Electroinitiation method: Pistoria, G. and O. Bagnarelli, *J. Polym. Sci. Polym. Chem. Ed.* 17: 1001 (1979); and Philips e a. *J. Polym. Sci. Polym. Chem. Ed.* 15: 1563 (1977).

One method of oligonucleotide probe disposition and immobilization preferred for use with unitary fiber optic arrays is the process known as photoactivaction; and employs one or more photoactivated monomer preparations in admixture with one species of oligonucleotide as a photopolymerizable formulation [as described in Munkholm et al., *Anal. Chem.* 58: 1427 (1986) and Jordan et al., *Anal. Chem.* 59: 437 (1987)]. Such monomer preparations typically comprise solutions of several monomers in admixture and a concentration of the chosen DNA or RNA oligonucleotide specie. A representative listing of different monomer compositions suitable for preparing an admixture which subsequently can be photopolymerized are given by Table 1 below.

It will be appreciated that the listing of Table 1 are merely representative of the many different substances which can be usefully employed in admixture with a specie of oligonucleotide. In addition, the scientific and industrial literature provides many alternative monomer preparations and admixtures which are also suitable for use in making the present invention. Accordingly, all of these conventionally known monomer preparations are considered to be within the scope of the present invention.

TABLE 1

| A. | Monomers |
|---|---|
| | acrylamide |
| | N,N-methylene bis (acrylamide) |
| | hydroxyethylmethacrylate |
| | EGDMA |
| | vinyl acetate |
| | (N-(3-aminopropyl) meth-acrylamide hydrochloride [Kodak, Inc.] |
| | N-acryloxy succinimide |

II. A Preferred Method Of Making A Biosensor

To demonstrate a most desirable method of making the biosensor comprising the present invention; and as a demonstration of the effectiveness for making optical determinations using the fully constructed fiber optic sensor, a detailed description of the manipulative steps for making a sensor able to hybridize in-situ with and consequently detect a mobile complementary oligonucleotide target specie bearing an identifying dye label is presented. It will be expressly understood, however, that the detailed description which follows hereinafter is merely illustrative and representative of the many different kinds of biosensors utilizing a unitary fiber optic array which can be made having one or more individual species of oligonucleotides deposited as multiple fixed probes at precise spatial positions on the optical array end surface, each disposed species-selective fixed probe being able to react with and individually hybridize with a labeled, mobile complementary target specie of oligonucleotide which is of interest in a fluid sample.

Surface silanization

Initially, fiber optic array similar to that illustrated by FIGS. 6–8 respectively was obtained from commercial sources [Applied Fiber Optics, Inc., Southbridge, Mass.]. One optical array surface was submerged in a acetone 10% solution of 3-(trimethoxysilyl) propyl-methacrylate dispersed in dry acetone and allowed to soak for 2 hours duration. After silanization, this optical array surface was rinsed first with dry acetone and then with distilled water.

Light Source

A fiber optic connector and ferrule [AMP, Inc., Harrisburg, Pa.] were modified to physically secure the fiber optic array to a fiber optic cable able to transport light energy of varying wavelengths to precise spatial positions on the distal array surface of the imaging fiber optic array. The exterior surface of one representative lighting cable is illustrated in an enlarged view by FIG. 9.

An inspection of the lighting cable of FIG. 9 reveals (in an exaggerated, highly oversimplified view for purposes of clarity) that the individual light sources via coordinated numerals correspond precisely to the spatial positions of FIGS. 7 and 8; and are directly aligned with individual fiber optical strands S1–S120 (which also are precisely positioned spatially and identifiable via linear coordinates). Thus, light originating from source L1 will be introduced only to fiber S1 spatially positioned at coordinate number "12a"; similarly, light energy emanating from source L85 will be introduced only to that precise spatial position on the proximal optical array end surface identifiable as fiber S85 at coordinates "4a". In this manner, only predetermined and prechosen fiber optical strands will receive light energy of determinable wavelengths for a specified duration; at a time desired by the user alone; and no other optical fiber strand will receive any light energy whatsoever other than those strands located at a precise spatial position on the surface of the optic array surface. By purposeful choosing, therefore, of which light sources on the lighting cable are to be employed, the user may introduce light energy at will to only prechosen, precise spatial positions and only to those few fiber optical strands known to be present at precisely that location alone on the optical array surface.

In most practical use instances, however, the lighting cable of FIG. 9 will not be employed because of its limitations. Recognizing that the typical cross-sectional diameter of a single fiber optical strand is only 2–20 micrometers; and recognizing further that the specie of oligonucleotide to be deposited precisely at a known spatial position on the optic array surface will desirably provide and encompass a surface area greater than the diameter of a single fiber strand; then clearly it is impractical and functionally unnecessary to employ only a lighting cable of such limited one-to-one correspondence as that shown by FIG. 9.

In actual practice, therefore, a lighting apparatus having a pinhole in a filter holder which allows fine focusing and precise placement of light is employed in the making of the sensor. This pinhole apparatus has only one light source of illumination rather than a cable having multiple light sources; and the single pinhole acts as a light source to introduce focused light energy to several dozen individually clad, optical fiber strands simultaneously—all the simultaneously illuminated strands being adjacently positioned within the imaging fiber optic array at precisely known spatial positions. In this manner, the single pinhole light source corresponds to and aligns with multiple fiber strands simultaneously; and permits the deposition of an oligonucleotide and monomer admixture over multiple strand faces simultaneously. The advantages and benefits of using the single source of focused lighting are that a controlled volume of admixture is precisely deposited at the pre-chosen spatial position on the optic array surface with minimal time and labor.

The lighting cable of FIG. 9, although completely operational for its intended purpose, is often far too cumbersome for practical use; is provided only as a representative article to demonstrate the principle of introducing light energy to a precise location on the proximal optic array surface; and is used merely to illustrate the method and the manner in which the dye becomes photopolymerized and precisely positioned at a prechosen location on the distal optic array surface. Having illustrated both the principle and the intended results, it will be recognized and appreciated that any lighting source of any correspondence with the fiber optical strands of the fiber optic array will serve so long as the disposed oligonucleotide specie deposits are spatially separate and spatially distinguishable from one another on the optic array surface.

Photopolymerization

The manipulations performed during photopolymerization are illustrated via FIGS. 10–15 respectively. For descriptive purposes only, the general magnified and oversimplified construction of the optic array surface of FIG. 7 and the lighting cable of FIG. 9 will again be used.

As seen within FIGS. 10–15, a fiber optical connector 130 and illumination source 140 provide the capability for illuminating specific areas of one optic array surface of the imaging fiber optic array described previously. Thus, the light energy photons emanating from the surface of the illumination source 140 of FIG. 10 are produced by only light sources L23, L24 and L34 respectively. Only light energy at those precise spatial positions is directed towards the proximal optic array surface 114 of the unitary fiber optical array 100. Consequently, as shown via FIG. 10 only those fiber optical strands located at spatial position coordinates 10k, 10l, and 9k respectively receive the light energy photons provided by the illumination source 140. Then as illustrated by FIG. 11, only those corresponding individually clad fiber optical strands S23, S24 and S34 convey the introduced light energy through the body of the unitary fiber optical array 100; and the light exits at the distal optic array end surface 112 only at precise spatial positions (that is, solely at coordinate numbers XK, XL, and IXK as seen within FIG. 7 above. It will be recognized and appreciated that no other spatial positions on the distal array end surface 112 are illuminated during this manipulation.

As the light energy photons emerge from the distal array end surface 112 at only the precise spatial positions indicated by FIG. 11, the optic array end surface 112 lies submerged in a prepared first monomer admixture. The light employed at only this precise spatial positions was prechosen to be at a set wavelength for photopolymerization and the optic array end surface was allowed to react with the first monomer preparation for approximately 30 seconds duration. The reactive contact between the first monomer admixture and the light energy initiated a photopolymerization reaction on the distal array end surface and caused a deposition and an immobilization of the first polymer zone only at those illuminated spatial positions. Thus, at the end of the allotted reaction time for photopolymerization, a discrete volume 150 of a polymer was deposited and immobilized solely on the distal optic array surface solely at spatial positions XK, XIK, and IXK. No other fiber strands were illuminated; no other fiber strands conveyed any light energy whatsoever; and no polymerization or deposition occurred at any other spatial positions. This is illustrated by FIG. 13.

After the first polymerization was completed, the illumination source 140 was then used again to illuminate the light positions corresponding to light position L15, L16, an L27. Light energy from only these positions introduced light energy photons precisely to the proximal optic array end surface 114 only at coordinate positions 10b, 10c, and 9c.

This caused the introduced light energy photons to be conveyed solely by fibers S15, S16 and S27. No other fiber strands were illuminated and no other fiber strands conveyed any light energy whatsoever. This is illustrated by FIGS. 13 and 14.

Consequently, as appears in FIG. 14, light energy photons carried by only these individually clad, fiber optical strands (S15, S16, and S27) cause the light to be conveyed and to exit from the distal optic array end surface 112 only at coordinate position numbers XB, XC, and IXC. The optic array surface was then immersed in a prepared second monomer mixture and the light energy allowed to react with the prepared mixture for a predetermined duration. During this reaction time, photopolymerization proceeded and the second zone was deposited solely at those spatial positions which were illuminated. In this manner, the multiple deposits of different polymer zones became immobilized by photopolymerization at only those precisely illuminated locations identifiable by the coordinate numbers XB, XC and IXC. At the end of the allotted time for reactive contact, the distal optic array end surface of the imaging fiber optic array was removed from the second monomer admixture and revealed the deposition of an immobilized deposit of a second polymer matrix at the precise spatial positions identifiable precisely by coordinate numbers XB, XC and IXC. A discrete polymerized cone-shaped deposit 160 of the second oligonucleotide specie is seen extending from the distal optic array end surface as illustrated by FIG. 15.

It will again be recognized and appreciated that under typical conditions the size of fiber core diameter in the fiber optic array so overwhelmingly exceeds the amount of corresponding cladding material that there is no effective separation between the fiber strands during the photopolymerization process. Thus the photopolymerization of the mixture at only the pre-chosen and illuminated spatial fluid positions results in the deposition of a single, unitary continuous volume large enough in surface area to encompass and cover multiple fiber end faces on the distal optic array surface. The presence of the cladding within the fiber optic array thus does not interfere with or hinder the continuity of the deposition. The result is both true and constant regardless of what specific process for depositing oligonucleotide species is employed and whether or not the favored photopolymerization technique is used.

The practitioner ordinarily skilled in this field will by now also recognize that there is no requirement or demand that an illumination fiber or cable as such be employed in this photoactivated method for making the sensor. To the contrary, one merely needs to introduce pinpoints of light into separate portions of areas of the imaging fiber optic array for photopolymerization to proceed. Thus, for example, one could achieve equivalent effects using lenses and/or lasers. Accordingly, any conventionally known means or manner of introducing light is deemed to be within the scope of the present invention.

The results of the completed photopolymerization process are illustrated by FIG. 15 in which the polymerized first oligonucleotide specie deposit 150 and the polymerized second oligonucleotide specie deposit 160 are individually located and identifiable at precise spatial positions on the distal optic array end surface. It will also be recognized that much of the distal optic array surface 112 remains unencumbered and unobscured; and that were additional light introduced at the proximal array end surface 114 at any of the unobscured strand spatial positions, such light photons would be conveyed and would exit from the distal optic array end surface 112 as unencumbered light energy which does not affect or influence the discrete deposits 150, 160 positioned separately

III. The Optical Sensing Apparatus And Instrumentation System

In order to be effectively employed, the prepared biosensor is combined with optical apparatus and instrumentation and is utilized as a system to detect and identify one or more specific analytes or peptide nucleic acids of interest. A generalized and representative optical apparatus and instrumentation system which is conventionally available and preferably employed is illustrated by FIG. 16.

Sensor measurements may be performed using the apparatus shown schematically by FIG. 16 in the following manner: White light from an excitation source 200 (such as an arc lamp) is collimated; focused by a lens 201; is passed through an excitation filter 202; and is focused on an optic sensor 205 via a 10× microscope objective 204. The optic sensor 205 is held in an xyz-micropositioner 206 which allows for fine focusing. Excitation light is transmitted and illuminates each thin film sensing receptor unit in the array of the sensor which individually fluoresces in proportion to analyte concentration. The returning fluorescence light is reflected 90° by the dichroic filter 203; desirably, but optimally passed through a beam splitter cube 208; filtered at an appropriate emission wavelength by emission filter wheel 210; and then is detected by the CCD camera 220. Ratiometric measurements are obtained by monitoring fluorescence while switching between two excitation filters 202 using the emission filer wheel 210. The CCD camera typically contains a photosensitive element and may be coupled to an electronic intensifier; which in turn is connected to a computer having a Video Frame Grabber graphic card that digitalizes and processes the video image. Visual imaging is achieved by using a CCD video camera to collect the light which is reflected 90° by the beam splitter cube. Illumination for visual imaging purposes is achieved either by rotating the excitation filter wheel to an empty position (using neutral density filters as necessary); or by illuminating the sample and its environs at the distal end of the sensor with an independent light source.

The optic sensing apparatus and instrumentation system shown by FIG. 16 detects fluorescence either as light intensity or as light wavelengths—that is, a spectral response generated by and released by a deposited probe from a single optical fiber strand end surface; or from at least one strand end face in a bundled array of single core fibers; or from at least one individual spatial position on the distal array end surface of the unitary array after initial illumination with light energy of a pre-determined wavelength. The light energy emitted or reflected from each fixed probe position individually is collected using a CCD video camera using standard frame grabbing technology and image processing capabilities. Each spectral response detected as emerging light energy by the detector of the CCD is recorded; and the pattern of fluorescence or color is shown either as energy wavelength or as light intensity pixels on the detector representing the spatial dimension. By definition, a pixel is a picture element—a sensitive region—which determines light intensity and/or light energy quantum.

IV. The Mobile Complementary Nucleic Acid Target Sequence

The analyte of interest to be detected optically using the biosensor and supporting apparatus is at least one mobile complementary oligonucleotide target specie bearing an identifying label joined directly or indirectly. The complementary target specie represents a sequence of nucleotides which corresponds as the complementary base sequence to the nucleic acids comprising the fixed oligonucleotide probe. It is expected and envisioned that the mobile complementary target specie will bind selectively to and hybridize in-situ with the nucleic acid sequence of the probe; and thereby generate a reaction product which is the result of specific and selective binding between only the fixed probe specie and the complementary target specie.

The present invention also intends and expects that an in-situ hybridization reaction will occur between each oligonucleotide specie deposit immobilized at one position or at multiple and differing spatial positions as fixed probes, each type of specie deposit reacting selectively with one mobile complementary oligonucleotide target specie (while other specie specific probes react concurrently with another alternative type of mobile complementary target specie). In this manner, different kinds of individually labeled complementary target species will react with only their counterpart and corresponding specie-specific fixed probes on at least one and preferably at several individual and differing spatial positions on the distal array end surface. Thus, at the user's choice and option, the array formats of the biosensor may be utilized to selectively detect only one mobile target species or a plurality of different target species intermixed in a fluid sample.

There are therefore only three requirements for each specie of complementary nucleic acid target to be detected using the present invention. These are: that the complementary target specie be mobile; that the complementary target specie ultimately bear a directly or indirectly joined identifying label; and that the complementary target specie be present in a fluid sample placed into reactive contact with the distal end of the biosensor. It will be noted and appreciated also that while there is no requirement as such, it is often desirable that the individual complementary oligonucleotide target specie be separated, isolated, purified or semi-purified before being placed into reactive contact in order for an effective in-situ hybridization to occur. Thus, the fluid sample often may comprise a mixture of different materials including not only multiple nucleic acid sequenced fragments, some of which are the complementary target specie for hybridization; but also may contain some extraneous matter, such as cellular debris or unrelated pharmacologically active molecules which typically are present only as incidental remnants from an earlier extraction, reaction, or preparation process. As a general rule, therefore, the fewer the number of extraneous chemical entities in the fluid sample, the faster the kinetics of in-situ hybridization will proceed.

The light energy absorbing dyes useful as joined identifying labels

At least one light energy absorbing dye is bound initially or becomes linked subsequently to each mobile complementary oligonucleotide target species as an identifying label. If desired, more than one dye reagent can be employed as a joined identifying label.

Each light energy absorbing dye formulation or composition will be bound directly or becomes linked indirectly to the one specie or to multiple different species of oligonucleotides intended for use as complementary targets. Moreover, each dye will then show evidence of its presence by either absorbing and reflecting a portion of the light energy; or, alternatively, by absorbing light energy and then subsequently emitting light energy of a different wavelength in return. Such reflected or emitted light energy is intended to be conveyed from the distal end surface; and such conveyed light will emerge from the proximal end surface for detection and measurement.

The various dyes which may be bound initially or linked subsequently to a chosen oligonucleotide fragment as a joined identifying label are all conventionally known and often commercially available. The present invention intends that all the commonly useful properties and capabilities of the various classes of light energy absorbing dyes be employed directly and indirectly, and as needed or desired for the specific use or application. Merely illustrative of the many different dyes are those fluorophores, indirect (secondary) labels, and interchelators listed below within Tables 2, 3, and 4 respectively.

TABLE 2

| Compounds | Excitation Wavelength (range or maximum) | Fluorescence emission range (max) |
|---|---|---|
| A. Fluorophores | | |
| Eosin | 520–530 nm | 530–580 nm (550 nm) |
| TRITC-amine | 555 nm | 570–619 nm (590 nm) |
| Quinine | 320–352 nm | 381–450 nm |
| Fluorescein W | 488–496 nm | 530 nm |
| Acridine yellow | 464 nm | 500 nm |
| Lissamine Rhodamine B Sulfonyl Chloride | 567 nm | 580 nm |
| Erythroscein | 504 nm | 560 nm |
| Ruthenium (tris, bipyridium) | 460 nm | 580 nm |
| Texas Red Sulfonyl Chloride | 591 | 612 |
| B-phycoerythin | 545, 565 nm | 575 nm |
| Nicotinamide adenine dinucleotide (NADH) | 340 nm | 435 nm |
| Flavin adenine dinucleotide (FAD) | 450 nm | 530 nm |
| Carboxy Seminaphthorhodafluor | 587 nm | 640 nm |
| Naphthofluorescein | 594 nm | 663 nm |
| Carboxy Fluorescein (Fam) | 495 | 520 |
| BODIPY | | |
| JOE | | |
| TAMRA | 540 | 564 |
| ROX | 567 | 591 |
| B. Fluorescent Antibody Conjugates | | |
| Protein A fluorescein conjugates | 480 nm | 520 nm |
| Anti-Atrazine fluorescein Conjugates | 480 nm | 520 nm |
| digoxin-Anti-digoxin Texas Red Conjugates | 590 nm | 615 nm |

TABLE 3

Secondary Label Pairs
(Labels include but are not limited to those mentioned in Table 2)

| | |
|---|---|
| Biotin | Labeled avidin/streptavidin |
| Protein A | Labeled IgG |
| Digoxin | Labeled anti-digoxin |
| Enzymes such as: | |
| alkaline phosphatase | diphosphate derivatives ELF-97 substrates |
| β-glucuronidase | |

TABLE 4

Intercalators ethidium bromide;
Cy-5;
Ru (byp)₂ MCCP;
Hoechst 33258 (bis-benzimide);
Cyanine dyes (for example TOTO ® series
(TOTO ®, YOYO ®, BOBO ™, POPO ™)
and SYBR I ®)

Note: TOTO ®, YOYO ®, BOBO ™, POPO ™ and SYBR I ® are trademarks of Molecular Probes Inc. (Eugene, Oregon).

It will be recognized and appreciated also that the available range, variety, and diversity of light energy absorbing dyes, dye formulations, and dye mixtures is not dependent upon a single light source or light energy supply in order to be effective. Although light energy of determinable wavelengths is desirably provided by electrical light sources—that is, light emitting diodes (LEDs), lasers, laser diodes and filament lamps whose bands of light energy are typically controlled and selected by filters, diffraction gratings, polarized filters; or alternatively broken into various broad wavelengths of light energy via prisms, lenses, or other optical/spectral articles, these are not exclusively the only source of useful light energy. Clearly, in various applications and circumstances other less typical light energy sources will also be useful. Accordingly, neither the true source, nor the nature of light energy photons, nor the manner in which they are conveyed or otherwise caused to be created is of importance or consequence.

In addition, the dye label individually may comprise a pair of specifically binding materials such as the chemical compounds listed within Table 3 for subsequent reactive contact and indirect juncture of an identifying label. Thus each dye label individually may in fact be formulated as a composite comprising light emitting dye in part; and include a variety of receiving elements which are able to interact as specific binding partners for joining the light energy dye label subsequently. Exemplifying some multiple formulations and combinations are those described below and used experimentally hereinafter.

Methods for ireiaring a mobile complementary target specie bearing an identifying label A range of different preparation methods and processes are conventionally known and available in the published scientific literature for creating a mobile complementary oligonucleotide target specie of known base sequence joined directly to an identifying label as a conjugate. Representative of and exemplifying these direct attachment procedures are the following: Agrawal et. al., *Nucleic Acids Res.* 14: 6227–6245 (1986); Smith et. al., *Nucleic Acids Res.* 13: 2399–2412 (1985); Cardullo et. al., *Proc. Natl. Acad. Sci. USA* 85: 8790–8794 (1988); *J. Fluorescence* 1: 135 (1991).

An alternative preparation strategy and procedure is exemplified by incorporation of biotin, in the form of a biotinylated nucleotide (such as biotin-d UTP) into the nucleic acid structure using conventional procedures such as nick translation or tailing [Rigby et.al., *J. Mol. Biol.* 113: 237 (1977); Lobban, P. E. and A. D. Kiser, *J. Mol. Biol.* 78: 453 (1973)]. The selective binding of the biotinylated targeted to the fixed probes in the in-situ hybridization reaction may then proceed in the absence of the dye label itself. Subsequently a conjugate complex constituted of avidin or streptavidin (proteins with a high affinity for binding to biotin) covalently are linked to a fluorescent or color reflecting dye ligand is then added as a dye label complex to the reaction fluid after hybridization has occurred; and the selective binding capability for the paired agents will then cause the identifying dye label to be joined via the avidin (or streptavidin) indirectly to each biotinylated target species wherever it is found. Qualitative and quantitative optical detection of the hybridized target specie can therefore be made on the basis of the spectral characteristics of the ultimately and indirectly joined identifying label. The listing of Table 3 provides other alternative pairs of specific binding agents suitable for use.

If desired, a biotinylated complementary target specie may be also prepared using polymerase chain reaction processing. The biotinylated amplified product obtained by PCR methodology may be used immediately or purified before being placed into reactive contact with the biosensor. Also, any of the other pairs listed in Table 3 may be substituted for use in the PCR method.

In addition, the user may optionally employ the technology known as enzymelabeled fluorescence (ELF) signal amplification to provide a joined identifying label. This technology is described in detail by U.S. Pat. Nos. 5,136,906 and 5,443,986, the texts of which are expressly incorporated by reference herein. In brief, an enzyme such as alkaline phosphatase is attached directly or is linked subsequently to the complementary oligonucleotide target species. The substrate for the enzyme's catalytic activity is one which provides an intense fluorescent signal and also demonstrates a very large Stoke's shift. Such substrates have been shown to be highly detectable labels when used with conventional in-situ hybridization method. See for example: *Am. J. Human Genet. Suppl.* 55, A271, Abstract #1588 (1994); *FASEB J.* 8: A1444, Abstract #1081 (1994); and *Mol. Biol. of the Cell Suppl.* 4 226a, Abstract #1313 (1993).

The user is thus given the option of preparing the complementary oligonucleotide target specie in several ways. The target specie nucleic acid sequence may be directly and immediately bound to an identifying dye label (such as those of Table 2) if desired. Alternatively, the complementary oligonucleotide target specie or species may be prepared as molecules having a receiving element such as biotin. The biotinylated target specie is allowed to hybridize in-situ with the fixed probes on the distal end surface of the biosensor; and then a prepared specific binding partner (such as avidin or streptavidin complex) bearing an identifying dye label as a component part can then be added to the reaction fluid after hybridization is completed—thereby causing the identifying label to be joined subsequently as well as indirectly to the immobilized hybridized reaction product. Finally, the intercalators (such as those listed within Table 4), may be used in unmodified form to label double-stranded, hybridized reaction products without any prior intermediate agent. The target species thus remains unlabeled throughout the entire hybridization process; the intercalators then will bind directly to the double-stranded reaction product upon reactive contact.

V. Identifying The Resulting, Species-Specific, In-Situ Hybridization Oligonucleotide Reaction Product The optical biosensor of the present invention intends and requires that a species-speciffic, in-situ hybridized reaction product result as the consequence of a selective reactive contact between a mobile complementary oligonucleotide target specie; a subsequently linked or directly joined identifying dye label; and one or more specie selective oligonucleotide probes deployed either on the distal end surface of a single optical fiber strand or at differing fixed spatial positions upon one array end surface of a unitary fiber optic array. Two features are essential for the biosensor: (a) The individual spatial positioning of the individual specie deposits as multiple fixed probes deployed on the distal end surface of the biosensor allows for a single or many different and distinct specie-specific, in-situ hybridizations to occur with a minimal volume of a mobile complementary oligonucleotide target specie having an initially existing or subsequently joined identifying label; and (b) the predetermined and fixed, individual spatial positioning(s) of the deployed, single specie, fixed probe(s) upon the discrete optic end surface utilize the initially or ultimately joined identifying label to identify the occurrence of a species-specific hybridization in-situ. Also each biosensor format relies upon spatial resolution as a means by which to differentiate and distinguish among the alternatively positioned hybridized complementary target species concurrently immobilized at many differing spatial locations on the optic array surface. In the fiber optic array format and in the bundle of fibers format, therefore, it is the combination of fixed spatial positionings for in-situ hybridization at the differing chosen locations and the spatial resolution capability to separate and distinguish the joined identifying dye label among the differing fixed surface positionings (and the different, hybridization reactions occurring concurrently) which avoids and eliminates random intermixing of individual light energy photons traveling to and from an identifying label concomitantly joined to each in-situ hybridized reaction product formed on the optic array surface of the biosensor.

Thus, within the in-situ hybridization zone on the distal end surface, each identifying label directly or indirectly joined to a hybridized complementary oligonucleotide target specie becomes, in turn, concomitantly immobilized and disposed only at individual probe locations fixed on the optic array end surface; and the presence of a joined identifying label held at any one or more fixed spatial positions can only be the sedondary consequence of a specie-specific in-situ hybridization reaction having occurred at that spatial position. Each immobilized identifying dye label will then show evidence of its presence at that precise spatial position by either absorbing and reflecting a portion of the light energy or absorbing light and then subsequently emitting light energy of a different wavelength in return. Such reflected or emitted light energy is conveyed via one or more individual fiber optic strands in aligned position with the immobilized dye itself. Such conveyed light will emerge from the other optic end surface only at precisely located spatial positions; and thus be distinguishable as such from other light energy conveyed by any other fiber optical strands via the precise spatial positioning and the spatial resolution of the emerging light at the optic array surface In this manner, the conventional limitations and demands of single channel optical fibers are eliminated since the strands within the fiber optical array retain the spatial positioning for each of the disposed dye labels. Thus, the traditional requirement for spectral resolution is removed due to the ability by the fiber optical array to resolve each of the dye labels spatially.

VI. Experiments And Empirical Data

Experimental Series A

Single optical fiber strand preparation

The distal and proximal faces of several single optical fiber strands are polished and cleaned. Each strand's distal end was silanized in 10% (amino) propyltriethoxysilane in acetone (v/v). The single core fiber strands were removed after 2 hours, rinsed with acetone, and then air dried for 30 minutes. The single core strands were placed in a 1.25% gluteraldehyde solution in 0.02 M phosphate buffer (pH 6.8) for 30 minutes. The single core fiber strands then were rinsed with distilled water and placed in 3% polyethyleneimine (PEI) in 0.02 M phosphate buffer (pH 6.8). Finally, the single core strands were air dried for 1 hour, rinsed, and stored in distilled water until being functionalized individually with oligonucleotides.

Bundled optical fiber array pretaration

To make a bundled optical fiber array, seven functionalized 200 µM diameter single core fiber strands were bundled together. The distal end surface of each fiber strand was first functionalized as described herein with a different cytokine oligonucleotide as a fixed probe—the bundling of seven individual strands creating a multi-target sensing array. The proximal ends of the bundled optical fiber array were epoxied into a 1 mm stainless steel tube (A) and placed into the fiber chuck of the epifluorescence imaging system as shown in FIG. 17. The bundled optical fiber array was three feet long in length and was used for remote sensing (B). The protective rubber tubing is removed from the distal end of the bundled arrays to enable individual functionalization (C).

Oligonucleotide preparation:

10 nmoles of 5'-amino-terminal oligonucleotide were dissolved in 90 µL of 0.1 sodium borate buffer (SBB). Oligonucleotide activation was initiated by adding 5 nmoles of cyanuric chloride in 10 µL of acetonitrile. The reaction proceeded at room temperature for 1 hour. Unreacted cyanuric chloride was removed by three cycles of centrifugal ultrafiltration (3000 d MW cutoff, Microcon 3, Amicon) and diluted with 200 µL of 0.1 M SBB. The activated primers were recovered in approximately 50 µL of 0.1 M SBB and stored at 4° C. Primers were used within one month of activation.

Single core fiber sensor Preparation:

The modified distal end of each single core strand was washed by dipping several times in five-2 ml changes of 0.1 M SBB. The distal strand tips were immersed in a 10 µL solution of 150 µL cyanuric chloride-activated oligonucleotide in 0.1 M SBB for 1–2 hours. The fiber strand tips were then immersed in 200 µL of 90% DMSO, 10% 1 M SBB buffer pH 8.3, 0.1 M succinic anhydride for 1 hour at room temperature. The fiber tips were washed (as described above) with 2 changes of 0.1 M SBB, 5 changes of TE (10 mMTris-HCl pH 8.3, 1 mM EDTA) containing 0.1 M NaCl and 0.1% SDS. Fibers tips were stored in the washing buffer until use.

Fluorescence measurements:

Fluorescence measurements were acquired with a modified Olympus epifluorescence microscope/charged coupled device camera described previously herein.

Primary PCR reaction:

A 176 base pair region from a human IL-4 cDNA plasmid clone [yokota et al., Proc. Natl. Acad. Sci. USA 83: 5894–5898 (1986)] was amplified using primers IL4-U (5-CATCGTTAGCTTCTCCTGA-3') and IL4-L (5'-AAAGTTTTGATGATCTCCTGTA-3') generating a double-stranded PCR product. Conditions for the reaction were 10 mM Tris-HCl pH 8.3, 50 mM KCl, 2.5 mM $MgCl_2$, 0.5% Tween-20, each primer at 0.5 µM dNTPs, 2 U Ampli-Taq polymerase, $10^4$ copies of BamHI-cleaved pcd-hIL4. Thermocycling parameters were 35 cycles consisting of 10 seconds at 94° C., 10 seconds at 55° C., and 30 seconds at 72° C.

Secondary PCR reaction:

The double-stranded primary amplification products were internally labeled during an asymmetric PCR step using fluorescein-labeled dGTP. Conditions for the reaction were 10 mM Tris-HCl pH 8.3; 50 mM KCl; 2.5 mM $MgCl^2$; 0.5% Tween-20; 1 µM unlabeled primer IL-4 L; 50 µM each dATP, dCTP, dTTP; 25 µM dGTP; 25 µM dGTP; 25 µM fluorescein-labeled dGTP. After asymmetric amplification, the reaction was extracted with phenol and isobutanol. Primers and nucleotides were removed by two cycles of centrifugal ultrafiltration (Microcon 30, Amicon 400 µL TE per wash). Samples were recovered from the filtration unit in 50 µL of TE.

PCR Product Assay

The array distal end was placed in 5 µL of 16 nM labeled PCR product in buffer (TE containing 0.1% SDS and 0.35 M NaCl) for 20 minutes then rinsed with buffer solution (TE containing 0.1% SDS and 0.35 M NaCl). Signal was acquired while the biosensor array was in buffer solution.

Experiment 1: The Biosensor

To create a DNA biosensor array, probes specific for human cytokine mRNA sequences were immobilized on the tips of single core optical fibers. Cytokines are powerful immune system hormones whose expression is stimulated in response to inflammatory stimuli or infection. For this reason, there is widespread interest in the regulation of the cytokine gene expression. The sequences of the cytokine probe and targets used are shown in Table E1.

To make a bundled optical fiber array, seven functionalized 200 µM diameter single core fibers were combined and bundled together using epoxy. The distal end surface of each optical fiber strand was first functionalized as described above with a different cytokine oligonucleotide as a fixed probe; and then the bundling of seven functionalized strands created a multi-target sensing array. The proximal ends of the bundled optical fiber array were then epoxied into a 1 mm stainless steel tube and placed into the fiber chuck (A) of the epifluorescence imaging system as shown in FIG. 17. The bundled array was three feet long in length and was used for remote sensing (B). The protective rubber tubing is removed from the distal end of the bundled array to enable individual functionalization (C).

The bundled array of optical fibers was then tested by placing the distal end of the bundled strand sensor into a solution containing one or more 5'-fluorescein-labeled cytokine sequences. The bundled array was removed from the target solution after incubation for 5 minutes and rinsed with buffer solution (TE, 0.1% SDS, 0.1 M NaCl). The bundled array was then placed in buffer solution and fluorescence signals were acquired (excitation wavelength 490 nm, emission wavelength 530 nm). Signal analysis was performed in less than 30 seconds with commercially available software (IP Lab Spectrum). The results are shown by FIG. 22.

The images of the bundled array biosensor in buffer solution as acquired by a CCD camera are shown by FIGS. 18A and 18B. The image with white light transmitted through the distal end of the array is demonstrated by FIG. 18A. In comparison, a background fluorescence image at 530 nm taken with 490 nm excitation in buffer solution is shown by FIG. 18B. While there is some light transmitted through the cladding, there is no fluorescence observed across the distal end surface of the bundled array.

TABLE E1

Probe Sequences

β-glo(+) (segment of human β-globin)
5'-($NH_2$—($CH_2$)$_{6-}$)TT TTT TTT TCA ACT TQA TCC ACG TTC ADD-3'

IFNG (interferon gamma 1)
5'-($NH_2$—($CH_2$)$_{6-}$)T12-TGG FTT CTC TGG GCT GTT ACT-3'

1L2 (interleukin-2)
5'-($NH_2$—($CH_2$)$_{6-}$)T12-TA CAA GAA TCC CAA ACT CAC CAG-3'

1L4 (interleukin 4)
5'-($NH_2$—($CH_2$)$_{6-}$)T12-CC AAC TGC TTC CCC CTC TGT-3'

1L6 (interteukin-6)
5'-($NH_2$—($CH_2$)$_{6-}$)T12-GT TGG GTC AGG GGT GGT TAT T-3'

Target Sequences

β-glo(+)-CF
5'-Fluorescein-TG AAC GTG GAT GAS GTT G-3'

IFNG-CF
5'-Fluorescein-AG TAA CAG CCA AGA GAA CCC AAA-3'

IL2-CF
5'-Fluorescein-CT GGT GAG TTT GGG ATT CTT GTA-3'

IL4-CF
5'-Fluorescein-AC AGA GGG GGA AGC AGT TGG-3'

IL6-CF
5'-Fluorescein-AA TAA CCA CCC CTG ACC CAA C-3'

Experiment 2

Background-subtracted mean fluorescence intensities were then obtained with IL-4 probe on the sensor. The bundled strand biosensor array was tested in different target solutions employing the sequences of probes and targets shown in Table E1. The biosensor was placed in a target solution for 5 minutes; rinsed with buffer solution (TE containing 0.1% SDS and 0.1 mM NaCl); and fluorescent images were then acquired with the fiber tip in buffer. The result is shown by FIG. 19.

The bundled strand array was dipped in 90% formamide in TE between each test to remove any hybridized target and to regenerate the sensor. The IL-4 target solution contained flurescein labeled oligonucleotide complementary to the IL-4 probe on the sensor. After hybridization and read-out, the sensor was regenerated and used to test the IL-2 and IFNGarget solutions containing fluorescein labeled targets that are not complementary to the IL-4 probe. As seen in FIG. 19, these targets do not hybridize to the sensor. The second IL-4 hybridization afforded a signal close to the original test.

Plots of background subtracted mean fluorescence at 530 nm were then taken with 490 nm excitation as a function of time using a 500 µm diameter single core sensor with β-glo probe. A kinetic study using 1 µM β-glo target solution is shown by FIG. 20. Also, a kinetic study using 0.1 µM µ-glo target solution is shown by FIG. 21. The sensor was placed in each of the µ-glo target solutions for a given time; rinsed with buffer solution (TE containing 0.1% SDS and 0.1 M NaCl); and a fluorescence signal was acquired with the sensor in buffer solution. After data acquisition, the fiber optic array biosensor was placed back in the target solution for an allofted time, rinsed, and examined in buffer. Once the kinetic data was acquired, the hybridized target was removed with 90% formamide in TE to regenerate the sensor.

Fluorescent images using the fiber optic biosensor array were acquired in buffer solution after treatment with IL2 target (A); IL4 target (B); IL6 target (C); β-glo target (D); IFNF target (E); and a mixture of IL4, IFNG and β-glo targets. The biosensor array distal end was placed sequentially in a fluid (A)–(F) using a 1 µM solution in TE containing 0.1% SDS and 0.1 M NaCl for 5 minutes; and was then rinsed with buffer solution (TE containing 0.1% SDS and 0.1 M NaCl). Hybridized oligonucleotides were removed after each immersion and optical detection using a 90% formamide solution in TE after each analysis. As shown by FIG. 22, the specificity of each probe-target hybridization (A)–(F) was confirmed. The signals obtained in buffer before hybridization were subtracted from the signals obtained after hybridization. High intensities are signified with white light.

The background subtracted mean fluorescence signals from FIG. 22 are shown in graph form by FIG. 23. Note: When a combination of oligonucleotide targets was placed in solution, the signal obtained was comparable to the signal obtained when a single target was in the solution. FIGS. 22 and 23 in combination reveal that high signals were only observed on those fibers carrying probes complementary to the added target, demonstrating that hybridization to the fiber is also highly specific.

Experiment 4

Hybridization competition between labeled and unlabeled variations of the same target sequences were performed using the biosensor array. Increasing concentrations of unlabeled targets were added to 1-µM solutions of a labeled identical target. The optical fiber biosensor was placed in the mixture of labeled and unlabeled target solution for 10 minutes; rinsed with buffer solution; and the background-subtracted fluorescence image was acquired while the distal array tip was in the buffer solution. The distal tip was rinsed with 90% formamide in TE between test samples to remove the hybridized target. The results are shown by FIG. 24; the fluorescence decrease was directly proportional to increasing concentration of sample target.

Experiment 5

A practical application of the fiber optic biosensor is shown by the assay of cDNA samples generated by reverse-transcription PCR (RT-PCR) [Egger, et al., *J. Clin. Microbiol.* 33: 142 (1995)]. A 176 base pair fragment containing the IL-4 probe sequence (Table E1) was amplified from a cloned IL-4 cDNA target, and internally labeled with fluorescein using an asymmetrical PCR procedure [Cronin et al., *Human Mutation* 7: 244–255 (1996)]. The cytokine sensor array was dipped directly into the purified PCR reaction mixture. Using 5 µL of a 16 nm PCR target solution the sensor gave a clear, detectable, specific signal after 20 minutes.

Optimization of the system

Immobilized probe concentrations limit the amount of complementary target that can hybridize to the probe and generate a signal. The feasibility of detecting a fluorescein labeled target in-situ hybridization to the immobilized probe on the distal surface was tested first using a 500 µm diameter single core fiber with an immobilized IL-4 probe (Table E-1). The tips of the array (surface area 0.002 cm2) were placed in the target solution, which can be as small as 3 µL in a 0.4 mL eppendorf tube. The detection system consists of a modified epifluorescence microscope with the optics optimized to couple with an optical fiber.

The detection system parameters were also optimized. Increasing the acquisition time improved the signal however, the increased exposure time caused photobleaching and adversely affected subsequent sensor use. A two second acquisition time was found to be optimal in maximizing the detection while minimizing photobleaching of the fluorescein-labeled target. This fiber optic biosensor system has a detection limit of 10 nM.

Characterization of the sensor

The sensor's specificity was evaluated by placing the sensor in complementary and non-complementary-labeled target solutions. The fluorescent signal increases upon exposure to the complementary labeled target. The complete absence of signal when the biosensor was placed in a non-complementary labeled targets confirmed the hybridization specificity (FIG. 19).

Lengthy incubation times are frequently a concern in hybridization experiments utilizing immobilized probes. The optical fiber biosensor described here shows excellent hybridization kinetics. Hybridization is 85% complete after 1 minute using a 1-µM target solution (FIG. 20). With a 0.1-µM target solution, hybridization is 90% complete after 15 minutes (FIG. 21). The 10-nM target solution required 10 minutes to generate a clear signal (data not shown).

Fiber biosensors can be regenerated repeatedly by dipping the distal array tip in 90% formamide in TE buffer (10 mM Tris-HCl pH 8.3, 1 mM EDTA) for 10 seconds at room temperature. The biosensor then gives an original comparable signal for all subsequent analyses with alternative complementary oligonucleotide target (FIG. 19). Heating the formamide solution to 45° C. was also effective and did not compromise sensor integrity.

The biosensor offers significant advantages for hybridization analysis. The optical fiber array serves as the hybridization support and also facilitates sensitive, quantitative fluorescent detection of in-situ hybridization using a very low sample volume. Multiple synthetic oligonucleotide probes were covalently immobilized and fixed on one end of a 200 μm diameter optical fiber.

The fiber optic biosensor and methodology demonstrates a fast, reproducible, highly sensitive and durable system for the specific identification of DNA sequences. Fiber optic biosensor arrays enable simultaneous detection of multiple DNA sequences with reduced assay time and increased convenience. Complete analysis of multiple DNA sequences can be accomplished in under 5 minutes. Biosensors can be prepared in advance and be stored at 40° C.; these maintain their sensing capabilities for many months. The biosensor's small size also offers the ability to perform hybridization analysis on large numbers of target sequences using extremely small sample volumes. The biosensor is also useful for performing in-situ hybridization analyses in settings where conventional hybridization methods would be difficult, if not impossible, to implement.

Experimental Series B
Experimental Protocol:

The approach to DNA immobilization involves the site-selective photodeposition of an acrylamide and N-acryloxysuccinimide copolymer. The distal face of a fiber optic imaging array is first functionalized with 3-trimethoxysilylpropylmethacrylate to attach the photopolymerizable acrylate to the glass and surface allowing for the covalent attachment of polymer matrices to the distal face. The proximal array end surface of the unitary array is placed on a photodeposition system which allows for site-positioned illumination of the proximal array end. The distal end of the functionalized array is then dip coated with a thin film of an acrylamide/acryloxysuccinimide prepolymer containing a photoinitiator. The prepolymer is then photopolymerized by light illumination through the fiber for a fixed time and excess prepolymer is removed by rinsing with ethanol. After the polymer matrix is deposited, the distal end is placed in a solution of a 5'-aminoterminated oligonucleotide. As the polymer then hydrates, the oligonucleotide reacts with the succinimidyl ester residue, thereby covalently immobilizing the oligonucleotide. The residual reactivity of the esters is capped by placing the distal end in a 1 mM ethanolamine buffer solution, pH 8.5. The process is subsequently repeated to immobilize other oligonucleotide probes. Once fabricated, the DNA sensor array is connected to a modified epifluorescence microscope (Olympus) with computer-controlled excitation and emission filter wheels and a frame-transfer charge coupled device (CCD) camera (Photometrics) as previously described herein.

Experiment 6

Initial studies were performed using a poly (dA) sensor array comprised of both an immobilized poly (dA) polymer matrix and a control acrylamide polymer matrix, which was not copolymerized with N-acryloxysuccinimide, using a poly (dT)-FITC target. The biosensor was placed directly in a dilute solution of poly (dT)-FITC. During hybridization of poly (dT)-FITC to the poly (dA) polymer matrix, poly-FITC concentrates in the polymer matrix resulting in an increase in fluorescence over the background solution fluorescence. The acrylamide matrix thus serves as a control for non-specific absorption of target. After hybridization to the poly (dT)-FITC, the poly (dA) biosensor array could be regenerated by immersing in 65° C. buffer for 15 minutes after hybridization. This procedure completely dehybridized the probe/target duplex. Table E2 lists the oligonucleotide probes used in this study along with the complementary target sequences.

TABLE E2

| Probe Name (code) | Sequence 5'-3' | Sequence 5'-3' | Target Name (code) |
|---|---|---|---|
| (p(dA)) | H2N-(a)$_{18}$ | FITC-(T)$_{18}$ | (p(dT)-FITC) |
|  |  | Biotin-(T)$_{18}$ | (p(dT)-biotin) |
| H-ras wild type (H-ras Wt.) | H2N-CCGGCGGTGT | FITC-ACACCGCCGG | Wild type target (Wt -FITC target) |
| H-ras mutant (H-ras Δ) | H2N-GCCGTCGGTGT | FITC-ACACCGACGGC | Mutant target (Δ-FITC target) |
|  |  | 5'-labeled biotin amplicon containing ACACCGACGGC | PRC amplicon Δ PCR) 109 bp |

FIG. 25 shows the fluorescence increase of the poly (dA) matrix upon repeat hybridizations to poly (dT)-FITC; and shows three repeat hybridizations after regenerating the poly (dA) sensor array with 65° C. buffer. The signal increases are essentially the same for all three hybridizations when the decrease in solution fluorescence is taken into account as measured with the acrylamide matrix control. The plot demonstrates that sensor regeneration occurs in less than 10 seconds, simplifying and speeding up the testing procedure.

The poly (dA) biosensor array was then tested for its time response to various concentrations of poly (dT)-FITC. This data is shown by FIG. 26. The sharp decrease between standards represents the biosensor regeneration with 65° C. buffer.

Other determinations were then made. FIG. 27 plots the initial hybridization rate versus poly (dT)-FITC concentration. The poly (dA) sensor array shows a linear response from 1.3–130 nM with an $R^2$ value of 0.99 demonstrating that the rate of hybridization is directly proportional to the concentration of the target oligonucleotide. This linearity indicates that the response time of the DNA sensor array is diffusion controlled; and that the oligonucleotide probes are immobilized on the surface of the polymer matrix; allowing for solution-type kinetics.

Experiment 7

A different labeling procedure was developed to increase the array's sensitivity and expand its generality. Presently PCR samples for fluorescence analysis must be labeled after amplification. However, PCR samples can be biotinylated during the amplification which decreases the time to analysis and minimizes sample contamination. The detection procedure involves hybridization with a biotinylated nucleic acid target followed by label juncture with streptavidin-FITC.

Accordingly, calibration of the poly (dA) matrix with poly (dT)-Biotin; and hybridization was carried out for 20 minutes at 0.2, 2.0 and 19.6 nM followed by development with streptavidin-FITC. The results are shown by FIG. 28 which plots the mean fluorescence intensity of the poly (dA) matrix versus the log of poly (dT)-biotin concentration. As in a diffusion controlled system, the fluorescence intensity is shown to be linear with the log poly (dT)-biotin concentration from 0.2–20 nM. This system has a detection limit approximately an order of magnitude lower in target concentration for the same in-situ hybridization time. This improvement is due to the multiple FITC labels on each streptavidin molecule and the absence of photobleaching during hybridization that otherwise occurs with FITC-labeled oligonucleotides. The technique has a detection limit of 0.2 nM which is approximately an order of magnitude lower than other DNA biosensors.

Experiment 8

In order to test if the DNA biosensor could distinguish single point mutations, an array comprised of multiple H-ras wild type probes (H-ras Wt.) and multiple mutant probes with a single base difference (H-ras Δ) was fabricated. A FITC-labeled mutant (Δ-FITC) target was hybridized to the DNA sensor array at 28° C. in low stringency buffer, 2×SSPE. The Δ-FITC target is the perfect complement for the immobilized H-ras Δ. The low stringency buffer condition was insufficient to distinguish the noncomplementary oligonucleotide target at 28° C.

As temperature is often utilized to distinguish non-complementary targets, thermal studies were then undertaken to determine the melt characteristics of the duplexes. The distal array end of the biosensor was immersed in buffer solution and the temperature was raised while monitoring fluorescence. FIG. 29 shows the melting curves of the DNA sensor array after hybridization at 28° C. with the Δ-FITC target. The plot shows that $T_m$ for the H-ras Wt./Δ-FITC target duplex occurs at approximately 42° C. while the $T_m$ for the perfect complement duplex H-ras/Δ-FITC target occurs at 55° C. The data shows that if hybridization is performed at approximately 54° C., only the complementary target will hybridize.

FIGS. 30A and 30B respectively show fluorescence images of the DNA sensor array after hybridization with the Δ-FITC target at 28° C. and 54° C., A and B respectively. The images indicate that the DNA sensor array can distinguish a point mutation when hybridization is conducted at 54° C. Images were acquired at 490 nm The DNA sensor array was then calibrated with the Δ-FITC target by the same procedure used for the poly (dA) sensor array and poly (dT)-FITC with the exception that hybridizations were carried out at 54° C. FIG. 31 shows hybridization data for the DNA sensor array to 196 nM Δ-FITC target at 54° C. The H-ras Wt. matrix showed no response to the H-ras Δ-FITC target.

FIG. 32 is a plot of the Δ target calibration curve for the data of FIG. 31 which demonstrates the sensitivity of the sensor in the concentration range 2.0 to 196 nM.

Experiment 9

In order to test the array's ability to distinguish point mutations of amplified DNA, a PCR sample containing the Δ target sequence was obtained. The target sample, biotinylated during PCR amplification, was first determined and diluted; allowed to hybridize to the DNA sensor array for 20 minutes at 54° C.; washed and then labeled by juncture to streptavidin-FITC.

FIG. 33 shows a fluorescence image of the DNA sensor array after a 20 minute hybridization to a biotinylated Δ PCR amplification at 54° C., followed by a 5 minute streptavidin-FITC development. The image was acquired at 490 nm excitation, 530 nm emission. The image of FIG. 33 demonstrates that the biosensor can distinguish single base mutations in amplified DNA.

A fiber optic DNA sensor array has been fabricated by photodeposition of amine-reactive polymer matrices on an imaging fiber optic array; and 5'-aminoterminal oligonucleotides have been covalently immobilized as multiple fixed probes through amide bond formation with the succinimidyl ester residues of the polymer matrices. This fiber optic DNA sensor array is capable of simultaneously monitoring multiple hybridization events. The DNA sensor array also has the added advantage of simultaneously evaluating a fluid mixture of target oligonucleotides with multiple kinds of probe oligonucleotides with real-time monitoring. The DNA sensor array can be utilized to identify a single point mutation of Ras oncogene PCR product; and the sensor optically detected point mutations at DNA concentrations of 0.2–196 nM following a 20 minute hybridization. Lower concentrations of target oligonucleotides could be detected by hybridizing for longer times. The biosensor's small size (350 μm o.d.) and the small volume of the individual array elements (20 pL) enable sub-microliter sample volumes to be analyzed, increasing the value of the sensor.

The present invention is not to be restricted in form nor limited in scope except by the claims appended hereto.

What we claim is:

1. An optical sensor for detecting nucleic aids in a fluid sample comprising:
   a preformed, unitary fiber optic array comprising a plurality of optical fiber strands, said strands being disposed co-axially and joined along their lengths, said fiber optic array having a proximal and a distal end;
   a polymer immobilized to at least a first and second portion of said distal end; and
   at least a first and a second nucleic acid attached to said polymer immobilized to at least a first and second portion of said distal end.

2. A sensor according to claim 1 wherein said nucleic acid is selected from the group consisting of DNA, RNA and PNA.

3. A sensor according to claim 1 wherein said preformed, unitary fiber optic array is selected from the group consisting of an imaging fiber, a coherent fiber array, a random fiber array, and a semi-random fiber array.

4. A sensor according to claim 1 further comprising a light source.

5. The sensor according to claim 4 further comprising a light detector.

6. A sensor acording to claim 1 wherein said first and second nucleic acid is attached to said polymer immobilized to at least a first and second portion of said distal end following polmerization of said polymer by introducing light energy to said multiple strand end faces at said proximal array end, said light enery introduced in the presence of a photactivatable compound.

7. A sensor according to claim 6 wherein said photoactivatable compound is selected from the group consisting of acrylamide, N,N-methylene bis (acrylamide), hydroxyethylmethacrylate, EGDMA, vinyl acetate, N-(3-aminopropyl) methacrylamide, hydrochloride, and N-acryloxy succinimide.

8. A sensor according to claim 1 wherein said first and second nucleic acids are attached to said polymer immobilized to at least a first and second portion of said distal end following polymerization of said polymer by introducing light energy to said multiple strand end faces at said distal array end, said light energy introduced in the presence of a photactivatable compound.

9. A sensor according to claim 8 wherein said photoactivatable compound is selected from the group consisting of acrylamide, N,N-methylene bis (acrylamide), hydroxyethylmethacrylate, EGDMA, vinyl acetate, N-(3-aminopropyl) methacrylamide, hydrochloride, and N-acryloxy succinimide.

10. A sensor according to claim 1 further comprising:
   at least one second nucleic acid attached to a polymer immobilized to at least one second portion of said distal array end.

11. A sensor according to claim 10 wherein said nucleic acid is selected from the group consisting of DNA, RNA and PNA.

12. A sensor according to claim 10 wherein said preformed, unitary fiber optic array is selected from the group consisting of an imaging fiber, a coherent fiber array, a random fiber array, and a semi-random fiber array.

13. A sensor according to claim 10 further comprising a light source.

14. The sensor according to claim 13 further comprising a light detector.

15. A sensor according to claim 10 wherein said first nucleic acid is attached to said polymer immobilized to said first portion of said distal end by introducing light energy to said multiple strand end faces at a first portion of said proximal array end, said light energy introduced in the presence of a photactivatable compound.

16. A sensor according to claim 15 wherein said photoactivatable compound is selected from the group consisting of acrylamide, N,N-methylene bis (acrylamide), hydroxyethylmethacrylate, EGDMA, vinyl acetate, N-(3-aminopropyl) methacrylamide, hydrochloride, and N-acryloxy succinimide.

17. A sensor according to claim 10 wherein said first nucleic acid is attached to said polymer immobilized to said first portion of said distal end by introducing light energy to said multiple strand end faces at a first portion of said distal array end, said light energy introduced in the presence of a photactivatable compound.

18. A sensor according to claim 17 wherein said photoactivatable compound is selected from the group consisting of acrylamide, N,N-methylene bis (acrylamide), hydroxyethylmethacrylate, EGDMA, vinyl acetate, N-(3-aminopropyl) methacrylamide, hydrochloride, and N-acryloxy succinimide.

19. A method of detecting at least one nucleic acid in a fluid sample comprising the steps of:
   a) providing a preformed, unitary fiber optic array comprising:
      i) a plurality of optical fiber strands, said strands being disposed co-axially and joined along their lengths, said fiber optic array having a proximal and a distal end; and
      ii) at least one first nucleic acid attached to a first polymer immobilized to a portion of said distal array end;
   b) contacting said distal end of said array with said sample fluid comprising at least one labeled complementary target nucleic acid; and
   c) detecting a complex comprised of said at least one nucleic acid and said at least one labeled target nucleic acid.

20. A method according to claim 19 wherein said array comprises a nucleic acid selected from the group consisting of DNA, RNA and PNA.

21. A method according to claim 19 wherein said array further comprises at least one second nucleic acid attached to a polymer immobilized to a second portion of said distal array end.

22. A method according to claim 21 wherein said array comprises a nucleic acid selected from the group consisting of DNA, RNA and PNA.

23. A method of making a fiber optic sensor comprising:
   a) providing a unitary fiber optic array comprising a plurality of optical fiber strands
   b) immobilizing a polymer to at least a first distal optical fiber strand end face by introducing light energy to said first optical fiber strand end face; and
   c) attaching said first nucleic acid to said immobilized polymer.

24. A method according to claim 23 wherein said light energy is introduced at the proximal end.

25. A method according to claim 23 wherein said light energy is introduced at the distal end.

26. A method according to claim 23 wherein said nucleic acid is selected from the group consisting of DNA, RNA and PNA.

27. A method according to claim 23 wherein said introducing light energy further comprises employing a light source and a masking means for illuminating a portion of said array end surface for precisely controlling the location and size of said polymer immobilization.

28. A method according to claim 23 further comprising:
   d) immobilizing a polymer to at least a second distal optical fiber strand end face by introducing light energy to said optical fiber strand end face; and
   e) attaching said second nucleic acid to said second immobilized polymer.

29. A method according to claim 28 wherein said nucleic acid is selected from the group consisting of DNA, RNA and PNA.

30. A method according to claim 28 wherein said introducing light energy further compises employing a light source and a masking means for illuminating a portion of said array end surface for precisely controlling the location and size of said polymer immobilization.

* * * * *

UNITED STATES PATENT AND TRADEMARK OFFICE
CERTIFICATE OF CORRECTION

PATENT NO. : 6,406,845 B1
DATED : June 18, 2002
INVENTOR(S) : David R. Walt et al.

It is certified that error appears in the above-identified patent and that said Letters Patent is hereby corrected as shown below:

Column 1,
Line 37, change "*Score*" to -- *Scope* --.

Column 3,
Line 22, after "DNA" insert a -- . --.

Column 5,
Line 8, change "insitu" to -- in situ --.
Line 46, change "onemand" to -- on-demand --.

Column 13,
Line 12, after "triangular form." insert the following sentence:
-- A sheath 41 may optionally be used to protect the unepoxied length 43 of the bundle. --

Column 15,
Lines 23 and 24, change "semio-herent" to -- semi-coherent --.

Column 16,
Line 67, change "nucleoti des" to -- nucleotides --.

Column 18,
Line 5, change "e a." to -- et al. --.

Column 23,
Line 52, change "dves" to -- dyes --.

Column 25,
Line 42, change "ireiaring" to -- preparing --.

Column 26,
Line 18, change "enzymelabeled" to -- enzyme-labeled --.

Column 27,
Line 37, change "sedondary" to -- secondary --.

Column 28,
Line 54, change "[yokota" to -- [Yokota --.

UNITED STATES PATENT AND TRADEMARK OFFICE
CERTIFICATE OF CORRECTION

PATENT NO.   : 6,406,845 B1
DATED        : June 18, 2002
INVENTOR(S)  : David R. Walt et al.

It is certified that error appears in the above-identified patent and that said Letters Patent is hereby corrected as shown below:

<u>Column 30,</u>
In Table E1, line 3, correct the sequence "TT TTT TTT TCA ACT TQA TCC ACG TTC ADD-3'" to -- TT TTT TTT TCA ACT TCA TCC ACG TTC ADD-3' --.

<u>Column 31,</u>
Line 12, change "IFNGarget" to -- IFNG-target --.
Line 23, change "$\mu$-glo" to -- $\beta$-glo --.
Line 28, change "allofted" to -- allotted --.

<u>Column 36,</u>
Line 56, change "polmerization" to -- polymerization --.

Signed and Sealed this

Fifth Day of August, 2003

JAMES E. ROGAN
*Director of the United States Patent and Trademark Office*